US012692323B2

(12) United States Patent
Yang et al.

(10) Patent No.: US 12,692,323 B2
(45) Date of Patent: Jul. 28, 2026

---

(54) VHH ANTIBODY FOR PCSK9 AND APPLICATION THEREOF

(71) Applicant: BGI SHENZHEN, Shenzhen (CN)

(72) Inventors: Naibo Yang, Shenzhen (CN); Xiaoyan Gao, Shenzhen (CN); Xinyang Li, Shenzhen (CN); Xinhua Zhang, Shenzhen (CN); Meiniang Wang, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 1024 days.

(21) Appl. No.: 17/818,631

(22) Filed: Aug. 9, 2022

(65) Prior Publication Data

US 2023/0091895 A1 Mar. 23, 2023

Related U.S. Application Data

(63) Continuation of application No. PCT/CN2020/074624, filed on Feb. 10, 2020.

(51) Int. Cl.
*C07K 16/40* (2006.01)
*A61P 3/06* (2006.01)
*A61K 39/00* (2006.01)

(52) U.S. Cl.
CPC ................ *C07K 16/40* (2013.01); *A61P 3/06* (2018.01); *A61K 2039/505* (2013.01); *C07K 2317/569* (2013.01)

(58) Field of Classification Search
None
See application file for complete search history.

(56) References Cited

U.S. PATENT DOCUMENTS 4,931,385 A * 6/1990 Block .............. G01N 33/54393
436/814
2019/0233542 A1 8/2019 Liu et al.

FOREIGN PATENT DOCUMENTS

| | | | |
|---|---|---|---|
| CN | 104169304 A | | 11/2014 |
| CN | 107840892 A | | 3/2018 |
| CN | 109897110 A | * | 6/2019 |
| WO | WO2018/054240 A1 | | 3/2018 |
| WO | WO2018/054241 A1 | | 3/2018 |

OTHER PUBLICATIONS

Chinese Office Action mailed Mar. 22, 2023 in Chinese U.S. Appl. No. 17/818,631.2, a corresponding foreign application of U.S. Appl. No. 17/818,631, 13 pages.

Essalmani et al., "A Single Domain Antibody Against the Cys- and His-rich Domain of PCSK9 and Evolocumab Exhibit Different Inhibition Mechanisms in Humanized PCSK9 Mice," Aug. 2018, Biological Chemistry, 399(12), 33 pages.

Weider et al., "Proprotein Convertase Subtilisin/Kexin Type 9 (PCSK9) Single Domain Antibodies are Potent Inhibitors of Low Density Lipoprotein Receptor Degradation," Aug. 2016, The Journal of Biological Chemistry, 291(32): 16659-16671.

Zhang, Changjiang, "Human Proprotein Convertase Subtilisin/ Kexin Type 9 Nanobodies Preparation," Jun. 2017. Dissertation, South China University of Technology. Guangzhou, China. 73 pages.

International Search Report and Written Opinion dated Nov. 16, 2020 in International Application No. PCT/CN2020/074624, 17 pages.

\* cited by examiner

*Primary Examiner* — Sharon X Wen

(74) *Attorney, Agent, or Firm* — Lee & Hayes, P.C.

(57) ABSTRACT

Disclosed is an antibody capable of specifically recognizing PCSK9 or an antigen-binding fragment thereof. The antibody comprises heavy chain variable region CDR1, CDR2, and CDR3 sequences shown in SEQ ID NO: 1, SEQ ID NO: 2, and SEQ ID NO: 3 or shown in amino acid sequences having at least 95% identity to SEQ ID NO: 1, SEQ ID NO: 2, and SEQ ID NO: 3. The antibody can specifically bind to PCSK9 and inhibit the activity of PCSK9.

20 Claims, 5 Drawing Sheets

Specification includes a Sequence Listing.

First round       Second round

VHH ANTIBODY FOR PCSK9 AND APPLICATION THEREOF

CROSS-REFERENCE TO RELATED APPLICATIONS

This application is a continuation of International Application No. PCT/CN2020/074624, filed on Feb. 10, 2020, the entire disclosure of which is incorporated herein by reference.

SEQUENCE LISTING INFORMATION

A computer readable xml file, entitled "Z030-0009US_Sequence Listing_ST26," created on or about Oct. 31, 2022, with a file size of about 78,848 bytes, contains the sequence listing for this application and is hereby incorporated by reference in its entirety.

TECHNICAL FIELD

The present disclosure relates to the field of biotechnology, in particular, to an antibody for PCSK9 and an application thereof, more particularly, to an antibody capable of specifically recognizing PCSK9 or an antigen-binding fragment thereof, a nucleic acid molecule, an expression vector, a recombinant cell, a pharmaceutical composition, a pharmaceutical use, and a kit for detecting PCSK9.

BACKGROUND

Cardiovascular diseases pose a serious threat to human beings, and are the leading cause of death for all human populations. Currently, statins, cholesterol absorption inhibitors, probucol, etc. are the main drugs in the market used for lowering cholesterol. Although statins have been shown to be effective in the treatment of cardiovascular diseases, with their widespread use, potential drawbacks have been identified. Firstly, patients treated with intensive statins still had a high residual risk of cardiovascular events, with a risk of incidence of 22.4% in 2 years; secondly, a large number of patients cannot tolerate statins, and especially for those with familial hypercholesterolemia, the goal of lowering the LDL-C concentration still cannot achieved even with treatment by the most effective statins at the maximum dose; most importantly, statins have a variety of side effects, such as causing abnormal blood glucose, muscle toxicity, memory and cognitive disorders, etc, with an incidence as high as 20%. Severe side effects may lead to rhabdomyolysis and acute renal failure, and a significant proportion of patients discontinue treatment due to the inability to tolerate the muscle pain caused by the side effects.

Proprotein convertase subtilisin/kexin type 9 (PCSK9), a novel proprotein convertase of subtilisin subfamily, is one of the important factors affecting autosomal dominant familial hypercholesterolemia. In addition to affecting the plasma cholesterol level and regulating neuronal apoptosis, PCSK9 has been found in research to be associated with inflammatory responses. Current research on PCSK9 mainly focused on the regulatory function of liver lipid metabolism. Previous studies have shown that PCSK9 can regulate liver lipid metabolism by promoting the degradation of low-density lipoprotein receptor (LDL-R) in hepatocytes, thus affecting the level of low-density lipoprotein cholesterol (LDL-C) in plasma. However, PCSK9 has two types of mutations, gain-of-function mutations and loss-of-function mutations.

Population studies have shown that several "gain-of-function" mutations of PCSK9 often occur in individuals with autosomal dominant hypercholesterolemia, while "loss-of-function" mutations of PCSK9 are associated with decreased plasma cholesterol. Individuals with loss-of-function mutations of PCSK9 have significantly reduced risk of coronary heart diseases. In 2005, Hobbs et al. reported in Dallas Heart Study that the LDL-C level in individuals with PCSK9 nonsense mutation gene would be lower than that in normal people by 28%; in 2006, Hobbs et al. published the effect of PCSK9 gene mutation on coronary heart diseases. Based on an atherosclerosis risk survey, they followed 9523 Caucasians and 3363 African-American people for up to 15 years, and found that the incidence of coronary heart disease in the population lacking 1 or 2 PCSK9 functional genes was significantly lower than that in the normal population. Copenhagen Heart Study found that functional deletion of the PCSK9 gene decreased the LDL-C level by 11% to 15% and decreased the coronary heart disease incidence by 6% to 46%. Zimbabwe et al. reported that deletion mutations in PCSK9 decreased the LDL-C level in African women by 27%. PCSK9 inhibitors offer a completely new treatment mode to combat LDL-C and are considered as the greatest advance in the lipid lowering field subsequent to statins. The advent of PCSK9 inhibitors brings hope for patients who have severe side effects when taking statins, and for patients whose statin therapy fails to achieve target LDL-C levels, such as patients with hereditary hypercholesterolemia.

Antibody drugs are the main direction of new drug research and development, and have been widely used in the field of infectious disease diagnosis, prevention and control, and biological science research. By 2015, 48 antibody drugs have been successfully marketed and 7 antibody drugs have been successfully approved only between April 2014 and March 2015. Six of the top 10 drugs sold worldwide in 2015 were antibody drugs. Since Hamers et al. found heavy chain antibodies with light chains naturally deleted in camel blood in 1993, Nanobody® (Nb) has gradually replaced other small antibodies and become a hot spot in the development of new antibody drugs. Nb is usually only about 15 KDa, which is about one-tenth of the size of traditional antibodies. Nb has disulfide bonds inside, and a large number of hydrophilic residues on the surface, and thus has strong resistance to heat and pH. The properties of Nb lacking the Fc segments and light chains enable Nb to recognize cryptic or small epitopes that cannot be recognized by traditional antibodies and avoid complement reactions; in addition, single domain antibodies have many advantages, such as high stability, low toxicity, strong solubility, easy target screening, easy expression in prokaryotic microorganisms, and good economy. Sequence homology analysis showed that the VHH germline gene sequence of Camel Nb was highly homologous to human VH3, but CDR1 and CDR3 of the Camel Nb were slightly longer than that in human, and CDR3 bulged outward in the tertiary structure, suggesting higher specificity and affinity for antigen binding. In view of the above advantages, Nb is being gradually developed as a monoclonal antibody drug for disease diagnosis and treatment, and is widely used in the development of enzyme inhibitors, and tumor, infection, and inflammation biological inhibitors. However, the small size of the nanobody provides many advantages for its therapeutic function, but small molecular proteins are easily eliminated in vivo. Transforming Nb into target enzyme, transmembrane protein or bivalent by genetic engineering can effectively improve antibody activity and stability, so as to achieve the purpose of research. In studies on inhibition of viral replication, it was found that the bivalent nanobody was at least 60 times more effective than the monovalent nanobody and had a longer duration of action in animals, effectively delaying the time of death in animals. Antibody drugs have great prospects, but domestic antibody drugs are still in the initial stage.

Antibody drugs are the main direction of new drug research and development, and have been widely used in the field of infectious disease diagnosis, prevention and control, and biological science research. By 2015, 48 antibody drugs have been successfully marketed and 7 antibody drugs have been successfully approved only between April 2014 and March 2015. Six of the top 10 drugs sold worldwide in 2015 were antibody drugs. Since Hamers et al. found heavy chain antibodies with light chains naturally deleted in camel blood in 1993, Nanobody (Nb) has gradually replaced other small antibodies and become a hot spot in the development of new antibody drugs. Nb is usually only about 15 KDa, which is about one-tenth of the size of traditional antibodies. Nb has disulfide bonds inside, and a large number of hydrophilic residues on the surface, and thus has strong resistance to heat and pH. The properties of Nb lacking the Fc segments and light chains enable Nb to recognize cryptic or small epitopes that cannot be recognized by traditional antibodies and avoid complement reactions; in addition, single domain antibodies have many advantages, such as high stability, low toxicity, strong solubility, easy target screening, easy expression in prokaryotic microorganisms, and good economy. Sequence homology analysis showed that the VHH germline gene sequence of Camel Nb was highly homologous to human VH3, but CDR1 and CDR3 of the Camel Nb were slightly longer than that in human, and CDR3 bulged outward in the tertiary structure, suggesting higher specificity and affinity for antigen binding. In view of the above advantages, Nb is being gradually developed as a monoclonal antibody drug for disease diagnosis and treatment, and is widely used in the development of enzyme inhibitors, and tumor, infection, and inflammation biological inhibitors. However, the small size of the nanobody provides many advantages for its therapeutic function, but small molecular proteins are easily eliminated in vivo. Transforming Nb into target enzyme, transmembrane protein or bivalent by genetic engineering can effectively improve antibody activity and stability, so as to achieve the purpose of research. In studies on inhibition of viral replication, it was found that the bivalent nanobody was at least 60 times more effective than the monovalent nanobody and had a longer duration of action in animals, effectively delaying the time of death in animals. Antibody drugs have great prospects, but domestic antibody drugs are still in the initial stage.

Therefore, it is of far-reaching and positive significance to develop domestic PCSK9 antibody inhibitors to meet the urgent domestic needs of antibody drugs.

SUMMARY

The present disclosure is based on the discovery and recognition of the inventors of the following facts and issues.

The development of PCSK9 antibodies in the related art focuses on murine traditional antibodies. However, traditional antibodies face difficulties in both mass expression and humanization, which are time-consuming and expensive, and the acquisition rate of effective antibodies is low, which seriously limits the development of PCSK9 antibody inhibitors. In particular, domestic antibody drugs are just in the early stage of development and cannot meet the needs of patients with cerebrovascular disease (CVD) at all.

According to the inventors of the present disclosure, camels were immunized with PCSK9 antigen, peripheral blood cells (PBMCs) of the immunized camels were collected to isolate PCSK9 affinity lymphocytes, total RNA was extracted, and the V region of the camel heavy chain antibody was cloned by Nest-PCR technology and inserted into a phage plasmid to construct a phage expression library. Then, the PCSK9 antigen was screened for multiple rounds by phage display technology. Finally, the screened high-affinity antibodies were expressed and purified in prokaryotic cells in large quantities to obtain single-domain antibodies, which were tested by enzyme-linked immunosorbent assay (ELISA) and surface plasmon resonance (SPR) to verify affinity and the binding constant. PCSK9 single domain antibodies with high affinity were successfully screened.

To this end, in a first aspect the present disclosure, disclosed is an antibody capable of specifically recognizing PCSK9 or an antigen-binding fragment thereof. According to some embodiments of the present disclosure, the antibody includes heavy chain variable region CDR1, CDR2, and CDR3 sequences shown in SEQ ID NO: 1, SEQ ID NO: 2, and SEQ ID NO: 3 or shown in amino acid sequences having at least 95% identity with SEQ ID NO: 1, SEQ ID NO: 2, and SEQ ID NO: 3.

```
                                    (SEQ ID NO: 1)
        GYTYSSNC.

(SEQ ID NO: 2)
        IYIGGGST.

(SEQ ID NO: 3)
        AVGCQGLVDFGY.
```

The heavy chain variable region CDR1 has an amino acid sequence shown in SEQ ID NO: 1 or an amino acid sequence with at least 95% identity with SEQ ID NO: 1; the heavy chain variable region CDR2 has an amino acid sequence shown in SEQ ID NO: 2 or an amino acid sequence with at least 95% identity to SEQ ID NO: 2; and the heavy chain variable region CDR3 has an amino acid sequence shown in SEQ ID NO: 3 or an amino acid sequence with at least 95% identity to SEQ ID NO: 3. According to some embodiments of the present disclosure, the antibody can specifically bind to PCSK9 and inhibit the activity of PCSK9.

According to embodiments of the present disclosure, the above-mentioned antibody may further include at least one of the following additional technical features:

According to some embodiments of the present disclosure, the antibody includes a heavy chain framework region sequence, at least a part of the heavy chain framework region sequence being derived from at least one of a camel antibody, a murine antibody, a human antibody, a primate antibody, or a mutant thereof.

According to some embodiments of the present disclosure, the heavy chain framework region sequence is derived from a camel antibody.

According to some embodiments of the present disclosure, the heavy chain framework region sequence has an amino acid sequence shown in any one of SEQ ID NOs: 4 to 15.

(SEQ ID NO: 4)
QVQLQESGGGSVQAGGSLRLSCTVS.

(SEQ ID NO: 5)
MGWFRQAPGKEHEGVAS.

(SEQ ID NO: 6)
YYADSVKGRFTISQDNAKNTVYLQMNSLKPEDTAMYYC.

(SEQ ID NO: 7)
WDQGTQVTVSS.

(SEQ ID NO: 8)
EVQLLESGGGLVQPGGSLRLSCAAS.

(SEQ ID NO: 9)
MGWVRQAPGKGLEWVSS.

(SEQ ID NO: 10)
YYADSVKGRFTISRDNSKNTLYLQMNSLRAEDTAVYYC.

(SEQ ID NO: 11)
EVQLLESGGGLVQPGGSLRLSCTVS.

(SEQ ID NO: 12)
MGWFRQAPGKEHEGVSS.

(SEQ ID NO: 13)
YYADSVKGRFTISQDNSKNTLYLQMNSLRAEDTAVYYC.

(SEQ ID NO: 14)
YYADSVKGRFTISQDNAKNTLYLQMNSLRAEDTAVYYC.

(SEQ ID NO: 15)
YYADSVKGRFTISQDNSKNTVYLQMNSLRAEDTAVYYC.

According to some embodiments of the present disclosure, the heavy chain framework region sequence has an amino acid sequence shown in any one of SEQ ID NOs:8 to 15. The inventors have made certain amino acid mutations to the heavy chain framework regions of the amino acid sequences shown in SEQ ID NOs: 4 to 7 to obtain the heavy chain framework regions of the amino acid sequences shown in SEQ ID NOs: 8 to 15. The inventors have found that the heavy chain framework regions of the amino acid sequences shown in SEQ ID NOs: 8 to 15 can significantly improve the degree of humanization of the antibody and reduce the immunogenicity of the antibody.

According to some embodiments of the present disclosure, the antibody has a heavy chain variable region having an amino acid sequence shown in any one of SEQ ID NOs: 16 to 25.

(SEQ ID NO: 16)
QVQLQESGGGSVQAGGSLRLSCTVSGYTYSSNCMGWFRQAPGKEHEGVA

SIYIGGGSTYYADSVKGRFTISQDNAKNTVYLQMNSLKPEDTAMYYCAV

GCQGLVDFGYWDQGTQVTVSS.

(SEQ ID NO: 17)
EVQLLESGGGLVQPGGSLRLSCAASGYTYSSNCMGWVRQAPGKGLEWVS

SIYIGGGSTYYADSVKGRFTISRDNSKNTLYLQMNSLRAEDTAVYYCAV

GCQGLVDFGYWDQGTQVTVSS.

(SEQ ID NO: 18)
EVQLLESGGGLVQPGGSLRLSCTVSGYTYSSNCMGWFRQAPGKEHEGVS

SIYIGGGSTYYADSVKGRFTISRDNSKNTLYLQMNSLRAEDTAVYYCAV

GCQGLVDFGYWDQGTQVTVSS.

-continued (SEQ ID NO: 19)
EVQLLESGGGLVQPGGSLRLSCAASGYTYSSNCMGWFRQAPGKEHEGVS

SIYIGGGSTYYADSVKGRFTISQDNSKNTLYLQMNSLRAEDTAVYYCAV

GCQGLVDFGYWDQGTQVTVSS.

(SEQ ID NO: 20)
EVQLLESGGGLVQPGGSLRLSCAASGYTYSSNCMGWFRQAPGKEHEGVA

SIYIGGGSTYYADSVKGRFTISQDNAKNTLYLQMNSLRAEDTAVYYCAV

GCQGLVDFGYWDQGTQVTVSS.

(SEQ ID NO: 21)
EVQLLESGGGLVQPGGSLRLSCAASGYTYSSNCMGWFRQAPGKEHEGVS

SIYIGGGSTYYADSVKGRFTISQDNAKNTLYLQMNSLRAEDTAVYYCAV

GCQGLVDFGYWDQGTQVTVSS.

(SEQ ID NO: 22)
EVQLLESGGGLVQPGGSLRLSCAASGYTYSSNCMGWFRQAPGKEHEGVS

SIYIGGGSTYYADSVKGRFTISQDNSKNTVYLQMNSLRAEDTAVYYCAV

GCQGLVDFGYWDQGTQVTVSS.

(SEQ ID NO: 23)
EVQLLESGGGLVQPGGSLRLSCTVSGYTYSSNCMGWFRQAPGKEHEGVS

SIYIGGGSTYYADSVKGRFTISQDNSKNTLYLQMNSLRAEDTAVYYCAV

GCQGLVDFGYWDQGTQVTVSS.

(SEQ ID NO: 24)
EVQLLESGGGLVQPGGSLRLSCTVSGYTYSSNCMGWFRQAPGKEHEGVS

SIYIGGGSTYYADSVKGRFTISQDNAKNTLYLQMNSLRAEDTAVYYCAV

GCQGLVDFGYWDQGTQVTVSS.

(SEQ ID NO: 25)
EVQLLESGGGLVQPGGSLRLSCAASGYTYSSNCMGWFRQAPGKEHEGVS

SIYIGGGSTYYADSVKGRFTISQDNAKNTLYLQMNSLRAEDTAVYYCAV

GCQGLVDFGYWDQGTQVTVSS.

According to some embodiments of the present disclosure, the antibody has a heavy chain variable region having an amino acid sequence shown in any one of SEQ ID NOs: 17 to 25. The inventors have found that antibodies having the heavy chain variable regions of the amino acid sequences shown in SEQ ID NOs: 17 to 25 are humanized to higher degrees and less immunogenic.

According to some embodiments of the present disclosure, the antibody further includes a heavy chain constant region, at least a part of the heavy chain constant region is derived from at least one of a murine antibody, a human antibody, a primate antibody, or a mutant thereof. Thus, the in vivo half-life of the antibody is further improved and the stability of the antibody is improved.

According to some embodiments of the present disclosure, a heavy chain constant region of the antibody is derived from a human IgG antibody or a mutant thereof.

According to some embodiments of the present disclosure, a heavy chain constant region of the antibody is derived from human IgG4.

According to some embodiments of the present disclosure, a constant region of the antibody has a full-length sequence shown in SEQ ID NO: 26.

(SEQ ID NO: 26)
PPCPSCPAPEFLGGPSVFLFPPKPKDTLMISRTPEVTCVVVDVSQEDPE

VQFNWYVDGVEVHNAKTKPREEQFNSTYRVVSVLTVLHQDWLNGKEYKC

KVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQE

GNVFSCSVMHEALHNHYTQKSLSLSPGK.

In the sequence shown in SEQ ID NO: 26, PPCPSCP (SEQ ID NO: 47) is a hinge region sequence, APE-FLGGPSVFLFPPKPKDTLMISRTPE-VTCVVVDVSQEDPEVQFNWYVDGVEVHNAKT KPREEQFN-STYRVVSVLTVLHQDWLNGKEYKCKVSNKGLPSSIE KTISKAK (SEQ ID NO: 48) is a constant CH2 region, and GQPREPQVYTLPPSQEEMTKNQVSLTCLVKGFYPS-DIAVEWESNGQPENNYKTTPPVLD SDGSFFLY-SRLTVDKSRWQEGNVFSCSVMHEALHN-HYTQKSLSLSPGK (SEQ ID NO: 49) is a constant CH3 region.

According to some embodiments of the present disclosure, the antibody has a heavy chain having an amino acid sequence shown in any one of SEQ ID NOs: 27 to 36.

(SEQ ID NO: 27)
QVQLQESGGGSVQAGGSLRLSCTVSGYTYSSNCMGWFRQAPGKEHEGVA

SIYIGGGSTYYADSVKGRFTISQDNAKNTVYLQMNSLKPEDTAMYYCAV

GCQGLVDFGYWDQGTQVTVSSPPCPSCPAPEFLGGPSVFLFPPKPKDTL

MISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSPG

K.

(SEQ ID NO: 28)
EVQLLESGGGLVQPGGSLRLSCAASGYTYSSNCMGWVRQAPGKGLEWVS

SIYIGGGSTYYADSVKGRFTISRDNSKNTLYLQMNSLRAEDTAVYYCAV

GCQGLVDFGYWDQGTQVTVSSPPCPSCPAPEFLGGPSVFLFPPKPKDTL

MISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSPG

K.

(SEQ ID NO: 29)
EVQLLESGGGLVQPGGSLRLSCTVSGYTYSSNCMGWFRQAPGKEHEGVS

SIYIGGGSTYYADSVKGRFTISRDNSKNTLYLQMNSLRAEDTAVYYCAV

GCQGLVDFGYWDQGTQVTVSSPPCPSCPAPEFLGGPSVFLFPPKPKDTL

MISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSPG

-continued

K.

(SEQ ID NO: 30)
EVQLLESGGGLVQPGGSLRLSCAASGYTYSSNCMGWFRQAPGKEHEGVS

SIYIGGGSTYYADSVKGRFTISQDNSKNTLYLQMNSLRAEDTAVYYCAV

GCQGLVDFGYWDQGTQVTVSSPPCPSCPAPEFLGGPSVFLFPPKPKDTLM

ISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSPGK

S.

(SEQ ID NO: 31)
EVQLLESGGGLVQPGGSLRLSCAASGYTYSSNCMGWFRQAPGKEHEGVA

SIYIGGGSTYYADSVKGRFTISQDNAKNTLYLQMNSLRAEDTAVYYCAV

GCQGLVDFGYWDQGTQVTVSSPPCPSCPAPEFLGGPSVFLFPPKPKDTL

MISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSPG

K.

(SEQ ID NO: 32)
EVQLLESGGGLVQPGGSLRLSCAASGYTYSSNCMGWFRQAPGKEHEGVS

SIYIGGGSTYYADSVKGRFTISQDNAKNTLYLQMNSLRAEDTAVYYCAV

GCQGLVDFGYWDQGTQVTVSSPPCPSCPAPEFLGGPSVFLFPPKPKDTL

MISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSPG

K.

(SEQ ID NO: 33)
EVQLLESGGGLVQPGGSLRLSCAASGYTYSSNCMGWFRQAPGKEHEGVS

SIYIGGGSTYYADSVKGRFTISQDNSKNTVYLQMNSLRAEDTAVYYCAV

GCQGLVDFGYWDQGTQVTVSSPPCPSCPAPEFLGGPSVFLFPPKPKDTL

MISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSPG

K.

(SEQ ID NO: 34)
EVQLLESGGGLVQPGGSLRLSCTVSGYTYSSNCMGWFRQAPGKEHEGVS

SIYIGGGSTYYADSVKGRFTISQDNSKNTLYLQMNSLRAEDTAVYYCAV

GCQGLVDFGYWDQGTQVTVSSPPCPSCPAPEFLGGPSVFLFPPKPKDTL

MISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVY

-continued

TLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSPG

K.

(SEQ ID NO: 35)

EVQLLESGGGLVQPGGSLRLSCTVSGYTYSSNCMGWFRQAPGKEHEGVS

SIYIGGGSTYYADSVKGRFTISQDNAKNTLYLQMNSLRAEDTAVYYCAV

GCQGLVDFGYWDQGTQVTVSSPPCPSCPAPEFLGGPSVFLFPPKPKDTL

MISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSPG

K.

(SEQ ID NO: 36)

EVQLLESGGGLVQPGGSLRLSCAASGYTYSSNCMGWFRQAPGKEHEGVS

SIYIGGGSTYYADSVKGRFTISQDNAKNTLYLQMNSLRAEDTAVYYCAV

GCQGLVDFGYWDQGTQVTVSSPPCPSCPAPEFLGGPSVFLFPPKPKDTL

MISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSPG

K.

According to some embodiments of the present disclosure, the antibody including the heavy chain having the amino acid sequence shown in any one of SEQ ID NOs: 27 to 36 has a high affinity to PCSK9, and has a prolonged half-life in vivo and higher stability.

According to some embodiments of the present disclosure, the antibody is a small molecule antibody.

According to some embodiments of the present disclosure, the small molecule antibody includes at least one of a nanobody, an Fab antibody, an Fv antibody, or a minimal recognition unit.

According to some embodiments of the present disclosure, the antibody is a nanobody. According to some embodiments of the present disclosure, the antibody, as a nanobody, has the advantages such as strong resistance to heat and pH, a higher affinity to the antigen PCSK9, high stability, low toxicity, strong solubility, easy direct expression in prokaryotic microorganisms, and good economy.

In a second aspect, the present disclosure provides a nucleic acid molecule. According to some embodiments of the present disclosure, the nucleic acid molecule encodes any one of the above-mentioned antibodies or antigen-binding fragments thereof.

According to some embodiments of the present disclosure, the above-mentioned nucleic acid molecule may further include at least one of the following additional technical features:

According to some embodiments of the present disclosure, the nucleic acid molecule is DNA.

According to some embodiments of the present disclosure, the nucleic acid molecule has a nucleotide sequence shown in any one of SEQ ID NOs:37 to 46.

(SEQ ID NO: 37)

CAAGTCCAGTTGCAGGAATCCGGTGGAGGATCTGTCCAGGCCGGTGGCTC

TTTACGTCTTAGTTGCACTGTGTCCGGCTATACGTACAGTTCCAACTGCATGGGTTGG

TTCAGACAAGCTCCCGGAAAGGAGCACGAGGGAGTAGCCTCAATTTACATCGGCGG

AGGCAGTACCTATTATGCAGATTCCGTCAAAGGTCGTTTTACGATCTCACAGGATAA

CGCAAAGAACACGGTCTACCTGCAAATGAACAGTCTGAAGCCCGAAGACACGGCAA

TGTATTATTGCGCCGTGGGTTGCCAAGGTTTGGTGGACTTCGGCTACTGGGACCAGG

GAACCCAGGTCACTGTATCATCC.

(SEQ ID NO: 38)

GAAGTTCAGCTGTTGGAATCAGGAGGTGGCCTTGTACAGCCTGGCGGCAG

TCTTCGTCTGTCTTGTGCCGCCTCTGGATACACTTACTCTAGTAATTGCATGGGTTGG

GTCAGGCAGGCCCCAGGAAAAGGATTGGAGTGGGTGTCATCCATTTACATCGGAGG

CGGATCTACTTACTACGCCGACTCCGTGAAGGGCAGGTTCACGATCTCCAGAGACA

ACTCCAAAAATACGTTGTACTTGCAGATGAACAGTCTTAGAGCTGAGGACACCGCA

GTTTACTACTGTGCCGTCGGTTGCCAGGGTCTAGTTGACTTTGGTTACTGGGATCAG

GGCACTCAGGTTACGGTTTCATCC.

(SEQ ID NO: 39)

GAAGTCCAGCTTTTGGAATCAGGCGGTGGACTAGTTCAGCCTGGTGGAAG

TCTGAGGCTGTCCTGCACAGTTTCCGGTTATACGTACTCCAGTAATTGCATGGGCTG

GTTCAGACAGGCCCCAGGTAAGGAGCACGAAGGTGTATCTTCTATTTACATTGGTGG

CGGATCTACTTACTACGCCGATTCAGTGAAGGGCCGTTTTACCATCTCCAGGGACAA

-continued

TAGTAAAAACACGTTGTACCTGCAGATGAACAGTTTAAGAGCAGAAGACACTGCTG

TCTACTACTGCGCCGTGGGTTGCCAGGGCTTGGTTGACTTCGGCTACTGGGACCAAG

GAACGCAGGTCACCGTATCTAGT.

(SEQ ID NO: 40)
GAAGTTCAATTACTTGAGAGTGGCGGTGGTTTGGTGCAGCCAGGCGGCTC

CCTGAGACTGTCATGCGCCGCTTCCGGATACACGTATTCTTCCAACTGCATGGGTTG

GTTCCGTCAGGCTCCTGGAAAGGAGCATGAAGGTGTCTCTTCAATCTACATAGGAGG

CGGTTCCACTTACTACGCAGACTCTGTGAAGGGCCGTTTTACCATCTCCCAGGATAA

TTCCAAGAACACATTGTACCTGCAAATGAACAGTCTACGTGCCGAAGACACAGCCG

TTTACTACTGCGCTGTTGGCTGCCAGGGCCTTGTGGACTTCGGCTATTGGGACCAAG

GCACACAGGTAACGGTTTCATCA.

(SEQ ID NO: 41)
GAGGTCCAGCTTCTTGAATCAGGCGGTGGACTAGTGCAGCCTGGCGGCTC

ATTGAGGTTGTCCTGTGCTGCCAGTGGCTACACGTACTCCTCCAACTGTATGGGCTG

GTTTAGGCAAGCACCCGGTAAAGAGCACGAGGGCGTAGCCTCTATCTACATTGGCG

GAGGATCTACCTATTACGCCGACTCCGTCAAAGGCCGTTTCACGATATCCCAGGATA

ACGCTAAGAACACGCTGTACTTACAAATGAACTCACTGAGAGCTGAAGACACCGCC

GTGTATTATTGCGCCGTTGGTTGTCAAGGTCTTGTCGACTTTGGATATTGGGATCAG

GGTACGCAAGTAACCGTCTCAAGT.

(SEQ ID NO: 42)
GAAGTTCAGTTGCTAGAGTCAGGAGGCGGTCTAGTCCAGCCCGGTGGATC

TCTGAGGCTAAGTTGCGCTGCCTCCGGTTACACGTATAGTTCAAACTGTATGGGATG

GTTTCGTCAAGCACCTGGTAAAGAGCACGAGGGTGTGAGTTCCATTTACATCGGCGG

TGGCAGTACATACTACGCAGATTCCGTTAAAGGCAGATTTACGATTTCTCAGGATAA

CGCCAAAAACACACTGTACCTACAAATGAACAGTCTTCGTGCAGAGGATACCGCAG

TGTATTATTGCGCCGTCGGATGCCAAGGTTTGGTGGACTTCGGCTATTGGGATCAGG

GCACGCAAGTTACCGTCTCTAGT.

(SEQ ID NO: 43)
GAAGTCCAACTTCTGGAGTCTGGCGGTGGCCTGGTACAACCTGGAGGCTC

ACTTAGGCTATCCTGCGCCGCTTCCGGCTATACATATTCTTCAAACTGTATGGGCTG

GTTTCGTCAGGCCCCAGGCAAAGAGCACGAGGGAGTATCATCAATCTACATTGGTG

GCGGCTCCACGTACTACGCCGATAGTGTGAAAGGCAGGTTCACCATCTCCCAGGAC

AACTCCAAGAACACTGTGTATCTACAAATGAATTCCCTGAGGGCTGAAGATACCGC

CGTATATTACTGCGCTGTTGGCTGCCAGGGCTTGGTTGATTTTGGCTATTGGGACCA

GGGCACACAGGTTACGGTGTCTTCC.

(SEQ ID NO: 44)
GAGGTCCAACTTTTGGAGTCTGGAGGAGGACTGGTCCAACCTGGAGGCTC

CCTGAGACTGTCCTGTACTGTGTCTGGCTACACCTACTCCAGCAACTGTATGGGCTG

GTTCAGACAGGCTCCTGGCAAGGAACATGAGGGAGTGTCCAGCATCTACATTGGAG

GAGGCAGCACCTACTATGCTGACTCTGTGAAGGGCAGGTTCACCATCAGCcaGGACA

ACAGCAAGAACACCCTCTACCTCCAAATGAACTCCCTGAGGGCTGAGGACACAGCA

GTCTACTACTGTGCTGTGGGCTGTCAGGGACTGGTGGACTTTGGCTACTGGGACCAG

GGCACCCAGGTGACAGTGTCCTCC.

-continued (SEQ ID NO: 45)
GAGGTCCAACTTTTGGAGTCTGGAGGAGGACTGGTCCAACCTGGAGGCTC

CCTGAGACTGTCCTGTACTGTGTCTGGCTACACCTACTCCAGCAACTGTATGGGCTG

GTTCAGACAGGCTCCTGGCAAGGAACATGAGGGAGTGTCCAGCATCTACATTGGAG

GAGGCAGCACCTACTATGCTGACTCTGTGAAGGGCAGGTTCACCATCAGCcaGGACA

ACgcCAAGAACACCCTCTACCTCCAAATGAACTCCCTGAGGGCTGAGGACACAGCAG

TCTACTACTGTGCTGTGGGCTGTCAGGGACTGGTGGACTTTGGCTACTGGGACCAGG

GCACCCAGGTGACAGTGTCCTCC.

(SEQ ID NO: 46)
GAGGTCCAACTTTTGGAGTCTGGAGGAGGACTGGTCCAACCTGGAGGCTC

CCTGAGACTGTCCTGTGCTGCCTCTGGCTACACCTACTCCAGCAACTGTATGGGCTG

GTTCAGACAGGCTCCTGGCAAGGAACATGAGGGAGTGTCCAGCATCTACATTGGAG

GAGGCAGCACCTACTATGCTGACTCTGTGAAGGGCAGGTTCACCATCAGCCAGGAC

AACgcCAAGAACACCCTCTACCTCCAAATGAACTCCCTGAGGGCTGAGGACACAGCA

GTCTACTACTGTGCTGTGGGCTGTCAGGGACTGGTGGACTTTGGCTACTGGGACCAG

GGCACCCAGGTGACAGTGTCCTCC.

The nucleotide sequence shown in SEQ ID NO: 37 encodes the heavy chain variable region shown in SEQ ID NO: 16, the nucleotide sequence shown in SEQ ID NO: 38 encodes the heavy chain variable region shown in SEQ ID NO: 17, the nucleotide sequence shown in SEQ ID NO: 39 encodes the heavy chain variable region shown in SEQ ID NO: 18, and the nucleotide sequence shown in SEQ ID NO: 40 encodes the heavy chain variable region shown in SEQ ID NO: 19, the nucleotide sequence shown in SEQ ID NO: 41 encodes the heavy chain variable region shown in SEQ ID NO: 20, the nucleotide sequence shown in SEQ ID NO: 42 encodes the heavy chain variable region shown in SEQ ID NO: 21, the nucleotide sequence shown in SEQ ID NO: 43 encodes the heavy chain variable region shown in SEQ ID NO: 22, the nucleotide sequence shown in SEQ ID NO: 44 encodes the heavy chain variable region shown in SEQ ID NO: 23, the nucleotide sequence shown in SEQ ID NO: 45 encodes the heavy chain variable region shown in SEQ ID NO: 24, and the nucleotide sequence shown in SEQ ID NO: 46 encodes the heavy chain variable region shown in SEQ ID NO: 25.

In a third aspect, the present disclosure provides an expression vector. According to some embodiments of the present disclosure, the expression vector carries the nucleic acid molecule as described above. After introducing the expression vector according to some embodiments of the present disclosure into a recipient cell, the aforementioned antibody is expressed under conditions suitable for protein expression, to obtain an antibody having high PCSK9 affinity activity.

According to some embodiments of the present disclosure, the above-mentioned expression vector may further include at least one of the following additional technical features.

According to some embodiments of the present disclosure, the expression vector is a prokaryotic expression vector. According to some embodiments of the present disclosure, the antibody is more readily expressed in pro-karyotic systems, and the expression of the antibody in prokaryotic systems can be further enhanced by selecting suitable prokaryotic expression vectors.

In a fourth aspect, the present disclosure provides a recombinant cell. According to some embodiments of the present disclosure, the recombinant cell carries a nucleic acid molecule as described above or expresses the antibody or the antigen-binding fragment thereof as described above.

According to some embodiments of the present disclosure, the above-mentioned recombinant cell may further include at least one of the following additional technical features.

According to some embodiments of the present disclosure, the recombinant cell is obtained by introducing the expression vector described above into a host cell.

According to some embodiments of the present disclosure, the expression vector is introduced into the host cell by electrical transduction.

According to some embodiments of the present disclosure, the recombinant cell is a prokaryotic cell.

In a fifth aspect of the present disclosure, the present disclosure provides a pharmaceutical composition. According to some embodiments of the present disclosure, the pharmaceutical composition includes the antibody, the nucleic acid molecule, the expression vector, or the recombinant cell as described above. According to some embodiments of the present disclosure, the pharmaceutical composition can specifically inhibit PCSK9, and is used for effectively treating or preventing PCSK9-related diseases with small side effects and long effective drug duration.

In a sixth aspect, the present disclosure provides the use of the antibody, the nucleic acid molecule, the expression vector, or the recombinant cell, or the pharmaceutical composition as mentioned above in the preparation of a medicament for the treatment or prevention of PCSK9-related diseases. The medicament is used for the treatment or prevention of PCSK9-related diseases with small side effects and long effective drug duration.

According to some embodiments of the present disclosure, the above-mentioned use may further include at least one of the following additional technical features.

According to some embodiments of the present disclosure, the medicament is used for the treatment or prevention of hyperlipidemia, hypercholesterolemia, and/or conditions caused by atherosclerosis, preferably cardiovascular diseases, stroke, or peripheral vascular diseases in mammals, preferably in human.

In a seventh aspect, the present disclosure provides a kit for detecting PCSK9. According to some embodiments of the present disclosure, the kit includes the antibody as described above. According to some embodiments of the present disclosure, the kit can be used for the specific detection of PCSK9.

In an eighth aspect the present disclosure, the present disclosure provides the use of the antibody, the nucleic acid molecule, the expression vector, or the recombinant cell as mentioned above in the manufacture of a kit for the detection of PCSK9 or the diagnosis of PCSK9-related diseases.

DESCRIPTION OF EMBODIMENTS

Figure 1:
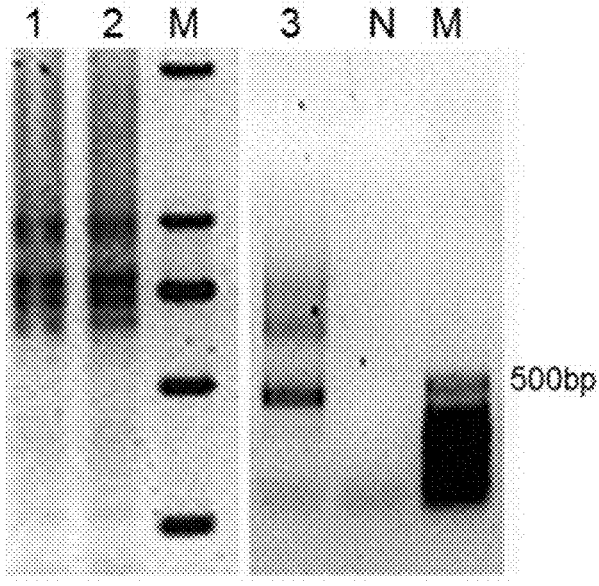
FIG. 1 is a photograph of gel electrophoresis for the identification of Nest-PCR-amplified VHH fragments of a camel heavy chain antibody according to some embodiments of the present disclosure.

The embodiments of the present disclosure are described below in detail. Examples of the embodiments are shown in the accompanying drawings. The same or similar numerals represent the same or similar elements or elements having the same or similar functions throughout the specification. The examples described below with reference to the accompanying drawings are illustrative, which are merely intended to explain the present disclosure, rather than to limit the present disclosure.

In describing the present disclosure, the terms used herein have been explained and illustrated merely to facilitate an understanding of the embodiments and are not to be construed as limiting the claimed solutions of the present disclosure.

Nanobody

As used herein, the term "nanobody" is a heavy chain antibody naturally lacking the light chain, found in camel blood, and including only the heavy chain (H chain) of a heavier molecular weight. Wherein, the amino-terminal (N-terminal) amino acid sequence of the peptide chain varies widely, and is referred to as a variable region (V region), and the carboxy-terminal (C-terminal) is relatively stable and varies little and is referred to as a constant region (C region). The V region of the H chain is referred to as VH. Some regions in the variable region, which have a higher degree of variation in the amino acid composition and arrangement order, are referred to as hypervariable regions (HVR). The hypervariable region is a site where an antigen binds to the antibody and is therefore also referred to as a complementarity-determining region (CDR). The heavy chain variable region has three CDR regions. CDR1 and CDR3 of camels are slightly longer than that of humans, and CDR3 protrudes outward in the tertiary structure, so it was inferred that the single domain antibodies have higher antigen binding specificity and affinity than the traditional antibodies.

According to the present disclosure, camels were immunized with PCSK9 antigen expressed by CHO cells to obtain anti-PCSK9 nanobody (Nb) with high specificity and high affinity. The antibody can specifically bind to PCSK9 antigen, and thus the antibody can be used for targeted treatment or prevention of hyperlipidemia and cardiovascular and cerebrovascular diseases.

In some embodiments, the present disclosure provides an antibody capable of specifically recognizing PCSK9 or an antigen-binding fragment thereof, the antibody contains at least one CDR sequence selected from the heavy chain variable region CDR sequences SEQ ID NOs: 1 to 3 or an amino acid sequence with at least 95% identity to the at least one CDR sequence selected from the heavy chain variable region CDR sequences SEQ ID NOs: 1 to 3. In some other embodiments, the antibody or the antigen-binding fragment provided herein has conservative amino acid substitution as compared to the heavy chain described above. The "antigen-binding fragment" refers to an antibody fragment that retains the ability to specifically bind to antigen (PCSK9). The "conservative amino acid substitution" refers to a substitution of an amino acid by an residue of another amino acid that is biologically, chemically, or structurally similar. The "biologically similar" means that the substitution does not destroy the biological activity of the PCSK9 antibody or the biological activity to the PCSK9 antigen. The "structurally similar" means that the amino acids have side chains of similar lengths, such as alanine, glycine, or serine, or have side chains of similar sizes. The "chemically similar" means that the amino acids have the same charge or are both hydrophilic or hydrophobic. For example, the hydrophobic residues isoleucine, valine, leucine, or methionine are substituted by each other. Alternatively, polar amino acids are used for substitution, such as arginine substituting lysine, glutamic acid substituting aspartic acid, glutamine substituting asparagine, and serine substituting threonine, etc.

In some embodiments, the present disclosure provides an antibody or an antigen-binding fragment. The an antibody or antigen-binding fragment has a heavy chain variable region having an amino acid sequence shown in any one of SEQ ID NOs: 16 to 25. The CDR regions (shown in SEQ ID NOs: 1 to 3) of the heavy chain variable region sequence of the antibody described above can be obtained by the inventors through antibody sequence alignment databases (NCBI, IMGT). In some other embodiments, the heavy chain variable region sequence of the antibody or antigen binding fragment has conservative amino acid substitutions as compared with the amino acid sequences shown in SEQ ID NOs: 16 to 25. Of course, these conservative amino acid substitutions do not alter the biological function of the antibody or antigen-binding fragment. In some embodiments, these conservative amino acid substitutions may occur to amino acids in the heavy chain variable region other than the CDR regions.

In some preferred embodiments, the present disclosure provides an anti-PCSK9 antibody having a heavy chain of an amino acid sequence shown in any one of SEQ ID NOs: 27 to 36.

In some preferred embodiments, the present disclosure provides an anti-PCSK9 nanobody having a heavy chain variable region of an amino acid sequence shown in any one of SEQ ID NOs: 17 to 25 or a heavy chain of an amino acid sequence shown in any one of SEQ ID NOs: 28 to 36.

Nucleic Acid Molecule, Expression Vector, and Recombinant Cell

In preparing or obtaining such antibodies, nucleic acid molecules expressing such antibodies can be linked to different vectors and then expressed in different cells to obtain the corresponding antibodies.

To this end, the present disclosure further provides an isolated nucleic acid molecule encoding the antibody or the antigen-binding fragment as described above.

In some embodiments, the isolated nucleic acid molecule has a nucleotide sequence shown in any one of SEQ ID NOs: 37 to 46.

In some embodiments, the isolated nucleic acid molecule has at least 90%, preferably 95% or more, more preferably 98% or more, or 99% or more homology with the nucleotide sequences shown in SEQ ID NOs: 37 to 46. The sequences with homology with the nucleotide sequences shown in SEQ ID NOs: 37 to 46 can express amino acid sequences similar to SEQ ID NOs: 16 to 25, so that the sequences can specifically bind to PCSK9 antigen to realize the targeting function of the antibody.

The present disclosure further provides an expression vector including the isolated nucleic acid molecule as described above. When the isolated polynucleotide described above is linked to a vector, the polynucleotide may be linked directly or indirectly to control elements on the vector, as long as the control elements are capable of controlling the translation, expression, etc. of the polynucleotide. These control elements may of course be derived directly from the vector itself or may be exogenous, i.e., not derived from the vector itself. Of course, the polynucleotide may be operably linked to a control element. As used herein, "operably linked" means that the exogenous gene is linked to a vector such that control elements within the vector, such as transcription control sequences and translation control sequences, etc. are capable of performing their intended function of regulating the transcription and translation of the exogenous gene. Of course, the polynucleotides used to encode the heavy chain of the antibody may be each independently inserted into a different vector, typically inserted into the same vector. Commonly used vectors may be, for example, plasmids, phages, and the like. For example, the Plasmid-X plasmid is used.

The present disclosure further provides a recombinant cell containing the expression vector. The expression vector can be introduced into prokaryotic cells to construct recombinant cells that can then be used to express the antibodies or antigen-binding fragments according to the present disclosure. By culturing the recombinant cells, the corresponding antibodies can be obtained.

Pharmaceutical Composition, Kit, and Pharmaceutical Use and Use in the Preparation of Kit.

The present disclosure further provides a pharmaceutical composition including the above-mentioned antibody or antigen-binding fragment and a pharmaceutically acceptable carrier.

The anti-PCSK9 antibodies provided herein can be incorporated into pharmaceutical compositions suitable for administration to a subject. Typically, these pharmaceutical compositions include an anti-PCSK9 antibody provided herein and a pharmaceutically acceptable carrier. As used herein, the term "pharmaceutically acceptable carrier" is intended to include any and all physiologically compatible solvents, dispersion media, coatings, antibacterial agents and antifungal agents, isotonic agents and absorption delaying agents, etc. Specific examples may be one or more of water, saline, phosphate buffered saline, dextrose, glycerol, ethanol, or combinations thereof. In many cases, isotonic agents such as sugars, polyols (e.g., mannitol, sorbitol) or sodium chloride, etc. are included in the pharmaceutical composition. The pharmaceutically acceptable carrier can, of course, include minor amounts of auxiliary substances such as wetting or emulsifying agents, preservatives or buffers, which serve to extend the shelf life or effectiveness of the antibody.

For example, the antibodies of the present disclosure can be incorporated into pharmaceutical compositions suitable for parenteral administration (e.g., intravenous, subcutaneous, intraperitoneal, intramuscular). These pharmaceutical compositions may be prepared in various forms, such as liquid, semi-solid, and solid dosage forms, including, but not limited to, liquid solutions (e.g., injection solutions and infusion solutions), dispersions or suspensions, tablets, pills, powders, liposomes, and suppositories. Typical pharmaceutical compositions are in the form of injection solutions and infusion solutions. The antibodies may be administered by intravenous infusion or injection or intramuscular or subcutaneous injection.

Of course, the anti-PCSK9 antibodies herein can also be formulated as a part of a kit or other diagnostic reagents as desired. According to some embodiments of the present disclosure, the present disclosure further provides a kit including the PCSK9 antibody described above. The kits provided by the present disclosure can be used, for example, in immunoblots, immunoprecipitations, and the like involving the kit for detection using PCSK9 antigen and antibody's specific binding properties. These kits may include any one or more of the following: an antagonist, an anti-PCSK9 antibody, or a drug reference material; a protein purification column; an immunoglobulin affinity purification buffer; assay diluent for cells; instructions or literature. Anti-PCSK9 antibodies can be used in different types of diagnostic tests, e.g. in vitro or in vivo detection of the presence of a wide variety of diseases or drugs, toxins or other proteins, etc. For example, the serum or blood of the subject may be detected to detect the related diseases. Such related diseases may include PCSK9-related diseases such as lipemia, hypercholesterolemia, and/or conditions resulting from atherosclerosis, cardiovascular disease, stroke or peripheral vascular disease, and the like. Of course, the antibodies provided herein can also be used in radioimmunoassays and radioimmunotherapies for the above diseases, and the like.

The anti-PCSK9 antibodies provided herein can be provided to a subject to treat the above diseases. To this end, the present disclosure provides a method for treating the above-mentioned diseases, including administering the antibody or the antigen-binding fragment thereof provided by the present disclosure to a subject in need thereof.

The technical solutions of the present disclosure will be explained below with reference to examples. Those skilled in the art will understand that these examples are illustrative only, and should not be considered as limiting the scope of the present disclosure. Examples, where specific techniques or conditions are not specified, are implemented in accordance with techniques or conditions described in the literature in the art or according to the product instructions. The used agents or instruments, which are not specified with the manufacturer, are conventional commercially-available products.

According to the present disclosure, eukaryotic expressed PCSK9 antigens were utilized to immunize camels to obtain a high quality PCSK9 immune nanobody library by flow cytometry sorting of affinity lymphocytes. The ELISA plate was coated with the PCSK9 antigen, the phage display technology was used to screen the antibody library of PCSK9 immune single domain antibodies, and then the screened single domain antibodies were transformed into *E. coli* expression systems for mass expression, so that the monoclonal single domain antibodies of PCSK9 with high affinity could be obtained in relatively short time.

Nine antibodies, VHH-Hu and VHH-Z 1 to VHH-Z 8 were designed independently according to the results of phage screening.

Example 1 Construction of PCSK9 Nanobody Phage Display Library (1) Immunization of Camel with PCSK9

1 mg of PCSK9 was mixed with an equal volume of Freund's adjuvant to 5 mL, the mixture was injected subcutaneously into the neck of camels at 3 to 5 points, and blood was collected from the auricular vein of the camels before immunization. The immunization was conducted once a month for a total of 4 times; 10 mL of peripheral blood was collected from the camels at each immunization. The camel head was fixed to one side during blood collection. The hairs on the skin at the blood collection site of the animal were shaved first and disinfected with 75% alcohol, and blood was collected after the alcohol was dried. The jugular sulcus was pressed with fingers, after the blood vessels were distended, the blood collection site was disinfected and injected with needles for blood collection. 10 mL of blood was collected into a 15 mL EDTA anticoagulant tube, which was immediately and continuously shaken slowly, mixed thoroughly, placed on ice, and transported back to the laboratory.

(2) Separation of Blood Lymphocyte Samples

Lymphocytes were separated from blood samples collected before and after each immunization by the following method:

i. 7 mL of lymphocyte separation liquid Ficoll was added into a 15 mL centrifuge tube;

ii. anticoagulant (EDTA) was added into fresh whole blood, followed by the addition of an equal volume of PBS (1×) or normal saline, and the mixture was mixed thoroughly;

iii. the 15 mL centrifuge tube added with the lymphocyte separation liquid (i.e., a centrifuge tube from step ii) was carefully and slowly transferred into another 15 mL centrifuge tube added with lymphocyte separation liquid (i.e., another centrifuge tube from step i, containing only the lymphocyte separation liquid), the above mixed liquid (formed in step ii) being placed on the liquid surface of lymphocyte separation liquid (namely, the two liquids did not mix, keeping a clear interface), followed by centrifugation at 3000 g for 20 min;

iv. the supernatant (plasma sample) was carefully transferred into a 1.5 mL cell cryopreservation tube with a 1 mL pipette, the tube written with the animal serial number and the word plasma was placed into a small cloth bag with string, and stored in a liquid nitrogen tank.

v. the leukocytes layer was carefully separated into a 15 mL centrifuge tube with a 1 mL pipette; the tube was fully filled with PBS (1×) to 15 mL; the leukocytes were washed with PBS (1×), the tube was centrifuged at 3000 g for 20 min, the supernatant was decanted carefully, without agitating the cell pellet at the bottom of the tube, and the leukocytes were recovered in the remaining 0.1 to 0.2 mL PBS.

vi. RNA later of 5 times the volume was added, the cell pellet was gently mixed and divided into 2 samples into 1.5 mL cell cryopreservation tubes which were stored in the liquid nitrogen tank.

(3) Extraction of Total RNA and Synthesis of cDNA 1 mL Trizol was added to one sample of cryopreserved lymphocytes, and let stand at room temperature for 10 min, the mixture was added with 0.2 mL of chloroform, followed by shaking vigorously and standing at room temperature to allow the solution to be stratified (about 10 min), after centrifugation at 12,000 rpm, the upper aqueous phase was collected, an equal volume of isopropanol was added, followed by blending and standing at room temperature for 15 min to allow the nucleic acid to precipitate, the mixture was centrifuged at high speed to remove the supernatant, 1 mL of 75% ethanol (prepared by DEPC water) was added to the RNA precipitate for washing, followed by centrifugation at high speed to remove the supernatant, the RNA was dried and dissolved in nuclease-free water, and 1 μL RNA solution was taken respectively for concentration and purity determination.

1 μg RNA was used for synthesis of cDNA using Super-Script™ III First-Strand Synthesis SuperMix (Invitrogen) kit, with Oligo dT as reverse transcription primer; and the synthesized cDNA was cryopreserved at −20° C.

(4) Construction of Phage Display Library

PCR Amplification:

The V region of camel heavy chain antibody (VHH) was amplified by Nest-PCR using the synthesized cDNA as template. The name and sequence of Nest-PCR primers are shown in Table 1.

TABLE 1

| primer information for amplification of camel VHH fragment | | |
|---|---|---|
| | Name | Sequence (5' to 3') |
| First round | CALL001 | GTCCTGGCTGCTCTTCTACAAGG (SEQ ID NO: 50) |
| | CALL002 | GGTACGTGCTGTTGAACTGTTCC (SEQ ID NO: 51) |
| | CALL005 | TGGTGGCAGGTCCCCAAGGT (SEQ ID NO: 52) |
| | CALL006 | TTCTTGGTGGCAGTAGCCGCAGT (SEQ ID NO: 53) |
| Second round | VHH-Back | GATGTGCAGCTGCAGGAGTCTGGRGGAGG (SEQ ID NO: 54) |
| | VHH-For | CTAGTGCGGCCGCTGGAGACGGTGACCTGGGT (SEQ ID NO: 55) |

PCR Reaction Conditions as Follows:
First Round

| cDNA | 2 μL |
|---|---|
| Mix | 12.5 μL |
| CALL001 | 0.5 μL |
| CALL002/006/007 | 0.5 μL |
| Water | make up to 25 μL |

Reaction conditions: 95° C., 5 min; 94° C., 1 min; 57° C., 1 min; 72° C., 1 min per cycle; 72° C., 7 min; amplication for 35 cycles in total.

Second Round

| Template | 40 ng |
|---|---|
| Mix | 25 μL |
| VHH For (10 uM) | 1 μL |
| VHH Back (10 uM) | 1 μL |
| Water | make up to 50 μL |

Reaction conditions: 95° C., 5 min; 94° C., 45'; 60° C., 45'; 72° C., 45' per cycle; 72° C., 7 min; amplication for 25 cycles in total.

After the PCR reaction, the PCR product was detected by 1.5% agarose gel electrophoresis. FIG. 1 showed the electrophoresis result of Nest-PCR. The target gene fragment of the first round of PCR was located at 700 bp, and the gel was cut to recover the target band. The target gene fragment of the second round of PCR was located at 500 bp, and the gel was cut to recover the target band, namely, the VHH fragment.

The VHH fragment and vector were double digested with restriction endonucleases NotI and PstI from NEB respectively, and the reaction systems were as follows:

Vector Digestion System:

| Vector | 20 μg |
|---|---|
| PstI | 10 μL |
| NotI | 20 μL |
| Cutsmart (Buffer) | 50 μL | add H₂O to 500 μL;
Fragment Digestion System:

| VHH Fragment | 5 μg |
|---|---|
| PstI | 7 μL |
| NotI | 14 μL |
| Cutsmart (Buffer) | 50 μL | add H₂O to 500 μL;

After digestion overnight at 37° C. and agarose gel electrophoresis, the gel was cut for recovery. The digested products of the vector and the VHH fragment were mixed and ligated with ligase from NEB at 16° C. overnight.

(5) Construction of Phage Display Library

The ligation product was purified by PCR Purification Kit (QIAGEN), 1 μL was taken to transform TG competent cells, the transformed cells were recovered at 37° C. for 2 h, and then diluted to $10^1$, $10^2$, and $10^3$ in a gradient manner. 300 μL of the diluted cells were plated and cultured overnight at 37° C. to calculate the number of clones, which was about $10^5$ clones/plate.

A large number of transformations were performed with the same transformation method described above, until the number of clones in the library reached $10^7$ or more. All clones were eluted with LB and centrifuged at 5,000 g for 5 min, the pellet was suspended in 2 mL LB, an equal volume of 30% glycerol was added, and the mixture was cryopreserved at −80° C.

Figure 2:
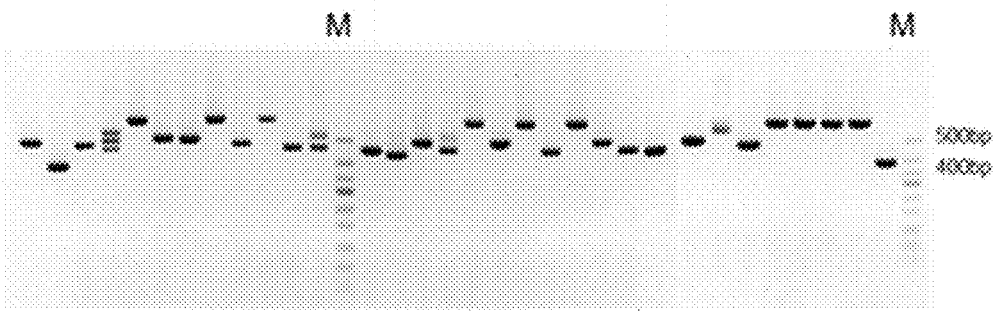
FIG. 2 is a photograph of gel electrophoresis results of PCR identification of recombination efficiency of VHH fragments in a constructed phage display library according to some embodiments of the present disclosure.

(6) Detection of Library Diversity:

Thirty clones of (5) were randomly picked and used as templates for the clonal PCR reaction, and the PCR product was detected by 1.5% agarose gel electrophoresis. As shown in FIG. 2, the recombination rate of the constructed PCSK9 nanobody library was 100%. The PCSK9 nanobody library was sequenced for analyzing the diversity, and the results showed that there were 13 amino acid sequences in 15 monoclonal antibodies, indicating that the constructed library had good diversity.

(7) Amplification and Rescue of Phage

Phage library of PCSK9 nanobody was amplified and rescued with helper phage. The monoclonal library preserved in (5) was inoculated into 100 mL culture medium and cultured to logarithmic growth phase, and helper phage with MOI of 20 was added, let stand at room temperature for 30 min, followed by low-speed centrifugation, the precipitate was suspended in culture medium and inoculated into 300 mL culture medium, followed by culturing overnight. The culture solution was centrifuged at 3,000 for 30 min next day, the supernatant was collected, PEG was added to precipitate phage, let stand on ice for 30 min, followed by centrifugation at 3,000 g for 30 min, the precipitate was PCSK9 nanobody phage library, the precipitate was suspended with PBS, and the titer was determined to be $2.9 \times 10^{12}$ pfu/mL.

Example 2 Elutriation of PCSK9 Nanobody Using Phage Display Technology (1) Elutriation of PCSK9 Nanobody Phage Library ELISA plates were coated with 100 ng PCSK9 antigen and incubated overnight at 4° C. On the next day, the rescued PCSK9 nanobody phages were added and incubated at room temperature for 2 h; the wells were washed with PBST for 10 times, 100 μL of triethylamine was added, the mixture was incubated at room temperature for 30 min, and the collected phages were the PCSK9 nanobody phage library obtained by elutriation; 10 μL of infected TG cells were plated to determine the number of clones screened, and the remaining phages screened were used for amplification.

(2) Amplification and Rescue of Screened Phage

The amplification and rescue methods were the same as in Example 1 (7). The obtained PBS suspension, i.e., the amplified phages after the first round of screening, was stored at 4° C. and used for the next round of screening; according to the same screening procedure as above, with a successively decreased amount of antigen, the screening was conducted for 3 to 4 rounds.

(3) ELISA Evaluation of Enrichment of Specific Antibodies

ELISA plate was coated with 100 ng of PCSK9 antigen at 4° C. overnight; on the next day, 2% BSA was added to conduct blocking at room temperature for 1 h. The phages amplified after each round of elutriation were added to the experimental group, and the same amount of wild-type phages were added to the control group, followed by incubation at room temperature for 2 h. The plate was washed with PBST 10 times to remove non-ligated phages; HRP-labeled anti-M13 antibody was added and the mixture was incubated at room temperature for 1 h; a chromogenic solution was added to react for 10 to 30 min in the dark; the absorbance was measured, which gradually increased with the number of times of bipanning, and tended to be stable in the third to fourth rounds of elutriation, indicating that the specific antibodies have been enriched.

(4) Identification of Nanobody Positive Clones Specific for PCSK9

Figure 3:
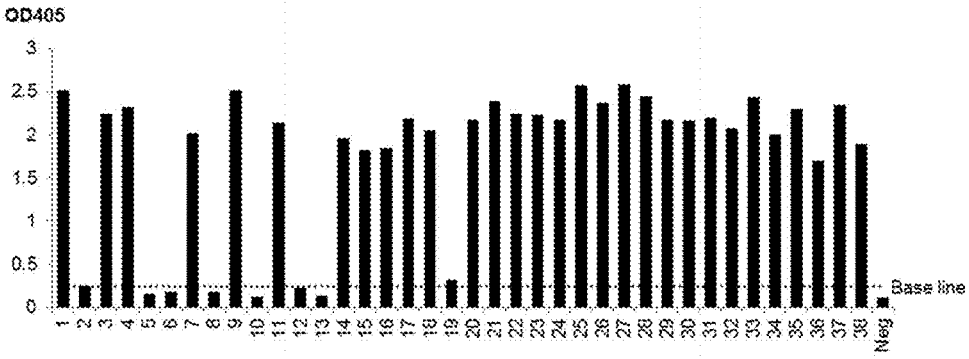
FIG. 3 is a graph showing the results of ELISA verification of elutriated PCSK9 single domain monoclonal antibodies according to some embodiments of the present disclosure.

ELISA plate was coated with 100 ng of PCSK9 antigen and incubated overnight at 4° C.; the phages obtained from the last round of screening were plated, 38 single clones were randomly picked, added to 1 mL culture medium, and cultured at 37° C. until logarithmic phase, and 1 mM IPTG was added to induce overnight; on the next day, the bacterial pellets were collected by centrifugation, then crushed, and centrifuged at 5,000 g for 15 min, and the supernatant was collected; at the same time, 2% BSA was added to the ELISA plate for blocking at room temperature for 1 h; the crushed monoclonal supernatant was added to each well of the experimental group, and the crushed blank TG superna-tant was added to the control group, followed by incubation at room temperature for 2 h. The plate was washed 10 times with PBST, mouse anti-HA tag antibody was added, and the mixture was incubated at room temperature for 1 h; the plate was washed 3 to 5 times with PBST, AP-labeled anti-mouse IgG antibody was added, and the mixture was incubated at room temperature for 1 h; the substrate was added for reaction 10 to 20 min, and the absorbance was read on the microplate reader; when the ratio of absorbance value of test well to absorbance value of control well was greater than 2.1 (Base line), it was determined as positive clone; the results of ELISA verification showed that 30 positive clones were obtained (FIG. 3).

(5) Analysis of Positive Clone Sequence

Figure 4:
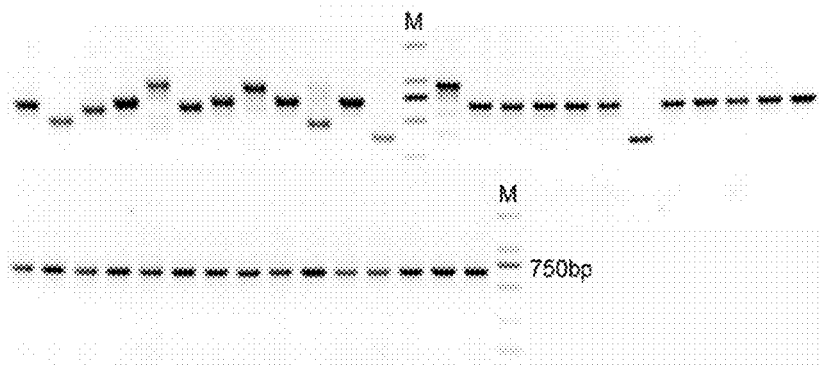
FIG. 4 is a graph showing the results of PCR verification of elutriated PCSK9 single domain monoclonal antibodies according to some embodiments of the present disclosure.

DNAs of the 30 positive clones obtained in (4) were extracted for verification of the insert by PCR, and as shown in FIG. 4, clones that were verified positive by PCR were subjected to sequencing analysis. Sequencing results showed that two nucleotide sequences were obtained and their amino acid sequences were analyzed. One of the two sequences had the structure of typical nanobody, i.e., consisting of framework regions (FR1, FR2, FR3, and FR4) and complementarity-determining regions (CDR1, CDR2, and CDR3).

The amino acid sequence of this monoclonal nanobody VHH4 was as follows:

```
                                        (SEQ ID NO: 16)
QVQLQESGGGSVQAGGSLRLSCTVSGYTYSSNCMGWFRQAPGKEHEGVA

SIYIGGGSTYYADSVKGRFTISQDNAKNTVYLQMNSLKPEDTAMYYCAV

GCQGLVDFGYWDQGTQVTVSS.
```

Amino acid sequences of framework regions (FR1 to FR4) and complementarity-determining regions (CDR1 to CDR3):

```
    FR1:
                                        (SEQ ID NO: 4)
    QVQLQESGGGSVQAGGSLRLSCTVS,

FR2 y
                                        (SEQ ID NO: 5)
    MGWFRQAPGKEHEGVAS,

FR3:
                                        (SEQ ID NO: 6)
    YYADSVKGRFTISQDNAKNTVYLQMNSLKPEDTAMYYC,

FR4:
                                        (SEQ ID NO: 7)
    WDQGTQVTVSS,

CDR1:
                                        (SEQ ID NO: 1)
    GYTYSSNC, sequence of CDR2:
                                        (SEQ ID NO: 2)
    IYIGGGST,
    and sequence of CDR3:
                                        (SEQ ID NO: 3)
    AVGCQGLVDFGY
```

In order to improve the humanization degree of nanobody and reduce immunogenicity, some amino acids of four framework regions of VHH4 were mutated to obtain nine antibody sequences, VHH-Hu and VHH-Z1 to VHH-Z8.

The antibody protein VHH-Hu of PCSK9 has the amino acid sequence: EVQLLESGGGLVQPGGSLRLSCAASGY-TYSSNCMGWVRQAPGKGLEWVSSIYIGGGST YYADSVKGRFTISRDNSKNTLYLQMNSLRAED-TAVYYCAVGCQGLVDFGYWDQGTQVT VSS (SEQ ID NO: 17), in which, the sequence of framework region 1 is EVQLLESGG-GLVQPGGSLRLSCAAS (SEQ ID NO: 8), the sequence of framework region 2 is MGWVRQAPGK-GLEWVSS (SEQ ID NO: 9), the sequence of framework region 3 is YYADSVKGRFTISRDNSKNTLYLQMNSLRAED-TAVYYC (SEQ ID NO: 10), the sequence of framework region 4 is WDQGTQVTVSS (SEQ ID NO: 7), the sequence of CDR1 is GYTYSSNC (SEQ ID NO: 1), the sequence of CDR2 is IYIGGGST (SEQ ID NO: 2), and the sequence of CDR3 is AVGCQGLVDFGY (SEQ ID NO: 3).

The antibody protein VHH-Z1 of PCSK9 having the amino acid sequence:

EVQLLESGGGLVQPGGSLRLSCTVSGY-TYSSNCMGWFRQAPGKEHEGVSSIY IGGG-STYYADSVKGRFTISRDNSKNTLYLQMNSLRAE-DTAVYYCAVGCQGLVDFGYWD QGTQVTVSS (SEQ ID NO: 18), in which, the sequence of framework region 1 is EVQLLESGG-GLVQPGGSLRLSCTVS (SEQ ID NO: 11), the sequence of framework region 2 is MGWFRQAPGKEHEGVSS (SEQ ID NO: 12), the sequence of framework region 3 is YYADSVKGRFTISRDNSKNTLYLQMNSLRAED-TAVYYC (SEQ ID NO: 10), the sequence of framework region 4 is WDQGTQVTVSS (SEQ ID NO: 7), the sequence of CDR1 is GYTYSSNC (SEQ ID NO: 1), the sequence of CDR2 is IYIGGGST (SEQ ID NO: 2), and the sequence of CDR3 is AVGCQGLVDFGY (SEQ ID NO: 3).

The antibody protein VHH-Z2 of PCSK9 has the amino acid sequence:

EVQLLESGGGLVQPGGSLRLSCAASGY-TYSSNCMGWFRQAPGKEHEGVSSI YIGGG-STYYADSVKGRFTISQDNSKNTLYLQMNSLRAE-DTAVYYCAVGCQGLVDFGYW DQGTQVTVSS (SEQ ID NO: 19), in which, the sequence of framework region 1 is EVQLLESGG-GLVQPGGSLRLSCAAS (SEQ ID NO: 8), the sequence of framework region 2 is MGWFRQAPGKEHEGVSS (SEQ ID NO: 12), the sequence of framework region 3 is YYADSVKGRFTISQDNSKNTLYLQMNSLRAED-TAVYYC (SEQ ID NO: 13), the sequence of framework region 4 is WDQGTQVTVSS (SEQ ID NO: 7), the sequence of CDR1 is GYTYSSNC (SEQ ID NO: 1), the sequence of CDR2 is IYIGGGST (SEQ ID NO: 2), and the sequence of CDR3 is AVGCQGLVDFGY (SEQ ID NO: 3).

The antibody protein VHH-Z3 of PCSK9 has the amino acid sequence:

EVQLLESGGGLVQPGGSLRLSCAASGY-TYSSNCMGWFRQAPGKEHEGVASI YIGGG-STYYADSVKGRFTISQDNAKNTLYLQMNSL-RAEDTAVYYCAVGCQGLVDFGYW DQGTQVTVSS (SEQ ID NO:20), in which, the sequence of framework region 1 is EVQLLESGG-GLVQPGGSLRLSCAAS (SEQ ID NO: 8), the sequence of framework region 2 is MGWFRQAPGKEHEGVAS (SEQ ID NO:5), the sequence of framework region 3 is YYADSVKGRFTISQDNAKNTLYLQMNSLRAED-TAVYYC (SEQ ID NO: 14), the sequence of framework region 4 is WDQGTQVTVSS (SEQ ID NO: 7), the sequence of CDR1 is GYTYSSNC (SEQ ID NO: 1), the sequence of CDR2 is IYIGGGST (SEQ ID NO: 2), and the sequence of CDR3 is AVGCQGLVDFGY (SEQ ID NO: 3).

The antibody protein VHH-Z4 of PCSK9 has the amino acid sequence:

EVQLLESGGGLVQPGGSLRLSCAASGY-TYSSNCMGWFRQAPGKEHEGVSSI YIGGG-STYYADSVKGRFTISQDNAKNTLYLQMNSL-

RAEDTAVYYCAVGCQGLVDFGYW DQGTQVTVSS (SEQ ID NO: 21), in which, the sequence of framework region 1 is EVQLLESGG-GLVQPGGSLRLSCAAS (SEQ ID NO: 8), the sequence of framework region 2 is MGWFRQAPGKEHEGVSS (SEQ ID NO: 12), the sequence of framework region 3 is YYADSVKGRFTISQDNAKNTLYLQMNSLRAED-TAVYYC (SEQ ID NO: 14), the sequence of framework region 4 is WDQGTQVTVSS (SEQ ID NO: 7), the sequence of CDR1 is GYTYSSNC (SEQ ID NO: 1), the sequence of CDR2 is IYIGGGST (SEQ ID NO: 2), and the sequence of CDR3 is AVGCQGLVDFGY (SEQ ID NO: 3).

The antibody protein VHH-Z5 of PCSK9 has the amino acid sequence:

EVQLLESGGGLVQPGGSLRLSCAASGY-TYSSNCMGWFRQAPGKEHEGVSSI YIGGG-STYYADSVKGRFTISQDNSKNTVYLQMNSL-RAEDTAVYYCAVGCQGLVDFGYW DQGTQVTVSS (SEQ ID NO: 22), in which, the sequence of framework region 1 is EVQLLESGG-GLVQPGGSLRLSCAAS (SEQ ID NO: 8), the sequence of framework region 2 is MGWFRQAPGKEHEGVSS (SEQ ID NO: 12), the sequence of framework region 3 is YYADSVKGRFTISQDNSKNTVYLQMNSLRAED-TAVYYC (SEQ ID NO: 15).

the sequence of framework region 4 is WDQGTQVTVSS (SEQ ID NO: 7), the sequence of CDR1 is GYTYSSNC (SEQ ID NO: 1), the sequence of CDR2 is IYIGGGST (SEQ ID NO: 2), and the sequence of CDR3 is AVGCQGLVDFGY (SEQ ID NO: 3).

The antibody protein VHH-Z6 of PCSK9 has the amino acid sequence:

EVQLLESGGGLVQPGGSLRLSCTVSGY-TYSSNCMGWFRQAPGKEHEGVSSIY IGGG-STYYADSVKGRFTISQDNSKNTLYLQMNSLRAE-DTAVYYCAVGCQGLVDFGYWD QGTQVTVSS (SEQ ID NO: 23), in which, the sequence of framework region 1 is EVQLLESGG-GLVQPGGSLRLSCTVS (SEQ ID NO: 11), the sequence of framework region 2 is MGWFRQAPGKEHEGVSS (SEQ ID NO: 12), the sequence of framework region 3 is YYADSVKGRFTISQDNSKNTLYLQMNSLRAED-TAVYYC (SEQ ID NO: 13), the sequence of framework region 4 is WDQGTQVTVSS (SEQ ID NO:7), the sequence of CDR1 is GYTYSSNC (SEQ ID NO: 1), the sequence of CDR2 is IYIGGGST (SEQ ID NO: 2), and the sequence of CDR3 is AVGCQGLVDFGY (SEQ ID NO: 3).

The antibody protein VHH-Z7 of PCSK9 has the amino acid sequence:

EVQLLESGGGLVQPGGSLRLSCTVSGY-TYSSNCMGWFRQAPGKEHEGVSSIY IGGG-STYYADSVKGRFTISQDNAKNTLYLQMNSL-RAEDTAVYYCAVGCQGLVDFGYWD QGTQVTVSS (SEQ ID NO: 24), in which, the sequence of framework region 1 is EVQLLESGG-GLVQPGGSLRLSCTVS (SEQ ID NO: 11), the sequence of framework region 2 is MGWFRQAPGKEHEGVSS (SEQ ID NO: 12), the sequence of framework region 3 is YYADSVKGRFTISQDNAKNTLYLQMNSLRAED-TAVYYC (SEQ ID NO: 14), the sequence of framework region 4 is WDQGTQVTVSS (SEQ ID NO: 7), the sequence of CDR1 is GYTYSSNC (SEQ ID NO: 1), the sequence of CDR2 is IYIGGGST (SEQ ID NO: 2), and the sequence of CDR3 is AVGCQGLVDFGY (SEQ ID NO:3).

The antibody protein VHH-Z8 of PCSK9 has the amino acid sequence:

EVQLLESGGGLVQPGGSLRLSCAASGY-TYSSNCMGWFRQAPGKEHEGVSSI YIGGG-STYYADSVKGRFTISQDNAKNTLYLQMNSL-RAEDTAVYYCAVGCQGLVDFGYW DQGTQVTVSS (SEQ ID NO:25), in which, the sequence of framework region 1 is EVQLLESGG-GLVQPGGSLRLSCAAS (SEQ ID NO: 8), the sequence of framework region 2 is MGWFRQAPGKEHEGVSS (SEQ ID NO: 12), the sequence of framework region 3 is YYADSVKGRFTISQDNAKNTLYLQMNSLRAED-TAVYYC (SEQ ID NO: 14), the sequence of framework region 4 is WDQGTQVTVSS (SEQ ID NO: 7), the sequence of CDR1 is GYTYSSNC (SEQ ID NO: 1), the sequence of CDR2 is IYIGGGST (SEQ ID NO: 2), and the sequence of CDR3 is AVGCQGLVDFGY (SEQ ID NO:3).

To increase the in vivo half-life of the antibody, nine Fc fusion antibodies, VHH-Hu-Fc and VHH-Z1-Fc to VHH-Z8-Fc, were obtained by fusing the Fc region of human IgG4, the sequence of which was shown below.

PPCPSCPAPEFLGGPSVFLFPPKPKDTLMISRTPE-VTCVVVDVSQEDPEVQFN WYVDGVEVHNAKTKPREEQFN-STYRVVSVLTVLHQDWLNGKEYKCKVSNKGLP SSIEK TISKAKGQPREPQVYTLPPSQEEMT-KNQVSLTCLVKGFYPSDIAVEWESNGQPEN-NYKTT PPVLDSDGSFFLY-SRLTVDKSRWQEGNVFSCSVMHEALHNHYTQK SLSLSPGK (SEQ ID NO: 26), in which, the sequence of the hinge region: PPCPSCP (SEQ ID NO: 47), the sequence of the constant CH2 region:

```
                                    (SEQ ID NO: 48)
APEFLGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPS

SIEKTISKAK,
```

The sequence of the constant region CH3 region:

```
                                    (SEQ ID NO: 49)
GQPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQKS

LSLSPGK
```

Example 3 Induced Expression and Purification of PCSK9 Nanobody (1) Construction of PCSK9 Nanobody Expression Bacteria Firstly, monoclonal PCSK9 nanobody was transferred to culture medium and cultured at 37° C. overnight. The plasmid was extracted with E.Z.N.A.® Plasmid Mini Kit I (OMEGA) on the next day, agarose gel electrophoresis and concentration determination were conducted, the plasmid containing the PCSK9 nanobody sequence was transformed into expression bacteria HB2151, then plated, and incubated overnight at 37° C.

(2) Induced Expression of PCSK9 Nanobody

On the next day, 5 clones were picked from the plate to verify by PCR whether the plasmid had been transformed into the expression bacterial strain; positive clones were picked, grown at 37° C. to an OD600 of 0.6 to 0.8, and induced for expression by addition of IPTG. The bacterial solution was centrifuged, the bacterial precipitate was collected, resuspended with lysis buffer, and sonicated, and the crushed bacterial supernatant was collected by centrifugation.

(3) Purification of PCSK9 Nanobody

Figure 5:
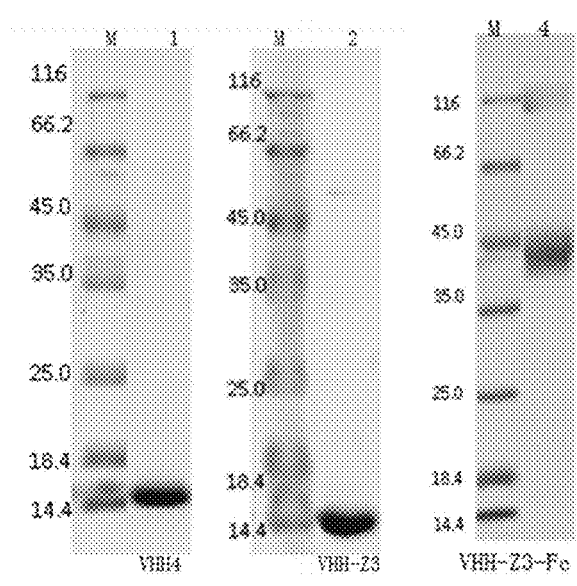
FIG. 5 is a graph showing the results of SDS-PAGE verification of expression and purification of PCSK9 single domain antibodies according to some embodiments of the present disclosure.

PCSK9 nanobody was obtained by Ni column affinity purification. The Ni column was washed first with ultrapure water and then with the lysis solution. The supernatant of the above-mentioned crushed PCSK9 nanobody expression bacteria was loaded to the Ni column at a flow rate of 1 mL/min; the impurity protein was removed by washing with 5 column volumes of affinity solution A (20 mM imidazole), then the target protein was eluted with an equal volume of affinity solution B (250 mM imidazole), and the eluent was collected; and finally the expression and purification of PCSK9 single domain antibodies were monitored by 15% SDS-PAGE (FIG. 5).

4. Construction of VHH-Fc Expression Vector

The target gene was amplified by PCR or gene sequence was synthesized by outsourcing; the target gene was inserted into a corresponding expression vector pCDNA3.4; a plasmid containing the correct sequence was obtained by sequencing; and the plasmid was subjected to enlarged production to be delivered downstream for expression.

(5) Expression of Mammalian Cells

HEK293 cells—HEK293 cells were subcultured with 293 serum-free CD medium (Sino Biological Inc., Cat. No. SMM 293-TI), and the plasmids to be expressed, VHH4-Fc and VHH-Z3-Fc, were mixed with transfection reagent TF2 (Sino Biological Inc., Cat. No. STF02) and then added to the cells, and 293 serum-free cell culture supplement (Sino Biological Inc., Cat. No. M293-SUFI-100) was added on days 1, 3, and 5 after transfection. Culture conditions for shake flasks: 5% $CO_2$, temperature 37° C., shaker speed 175 rpm.

(6) Purification

The culture solution was centrifuged at 6000 rpm for 20 min, and filtered with a filter, and the supernatant was taken.

a. Pretreatment of Chromatographic column: the ProteinA affinity chromatography column was washed with ultrapure water and then equilibrated with equilibration buffer;

b. Loading and equilibration: the solution was loaded into the ProteinA affinity chromatography column, and after the loading, the column was drip washed with an equilibration buffer until the baseline was stable;

c. Elution: the column was eluted with Elution3.0 (0.1M citric acid), the eluting peak was collected, followed by neutralization with 2M Tris;

d. The ProteinA affinity chromatography column was regenerated;

e. The sample was purified by desalting with a suitable buffer.

f. After sterile filtration of the purified sample, the retained sample was submitted for QC.

Figure 6:
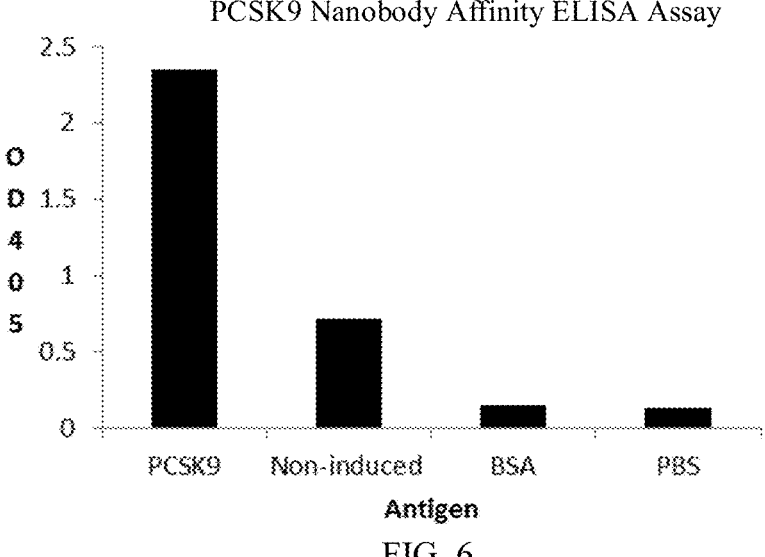
FIG. 6 is a graph showing the results of ELISA verification of affinity of purified PCSK9 single domain antibodies according to some embodiments of the present disclosure.

Example 4 Determination of Affinity of PCSK9 Antibody (1) Analysis of Affinity of PCSK9 Nanobody by ELISA Assay 100 ng of PCSK9 protein was used in the experimental group, non-induced plasmid-expressed protein was used in the control group, BSA was used to coat the ELISA plates, and the plates were incubated at 4° C. overnight. On the next day, 2% BSA was added to conducting blocking at room temperature for 1 h; the purified PCSK9 antibody was added into the control group and the experimental group, and PBS was added into the blank group, and the plates was incubated at room temperature for 2 h. The plated was washed 10 times with PBST, secondary antibody was added, and the mixture was incubated at room temperature for 1 h; the substrate was added to react 10 to 20 min and absorbance was read on a microplate reader. The results of ELISA assay (FIG. 6) showed that PCSK9 nanobody had good affinity for PCSK9, with the binding activity much higher than that in control group.

(2) SPR Analysis of Binding Constant for PCSK9 Nanobody

Figure 7:
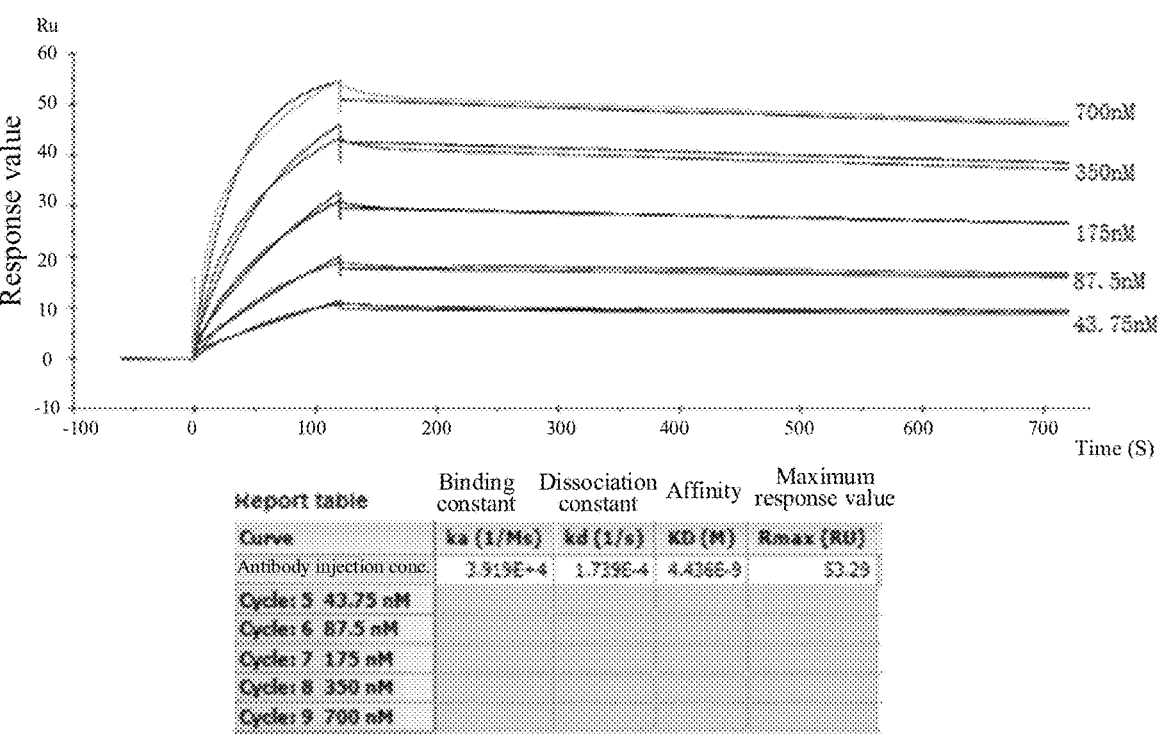
FIG. 7 is a graph showing the results of SPR assay for VHH4 affinity according to some embodiments of the present disclosure.
Figure 8:
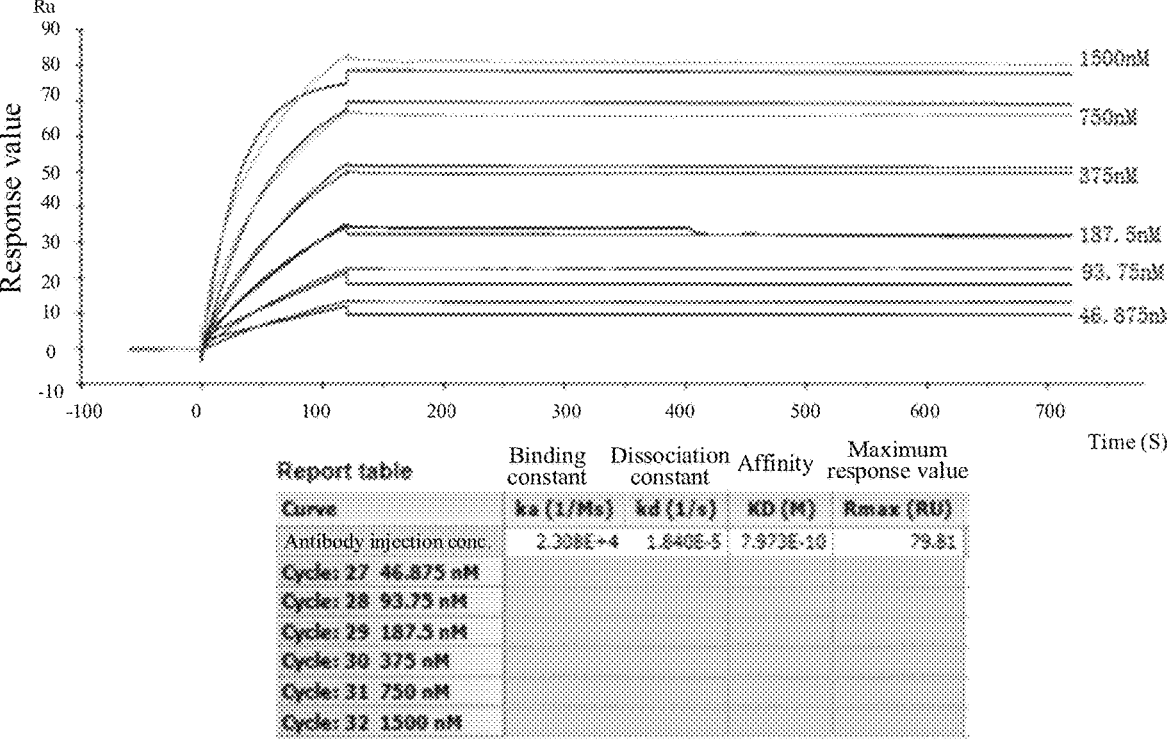
FIG. 8 is a graph showing the results of SPR assay for VHH-Z3 affinity according to some embodiments of the present disclosure.
Figure 9:
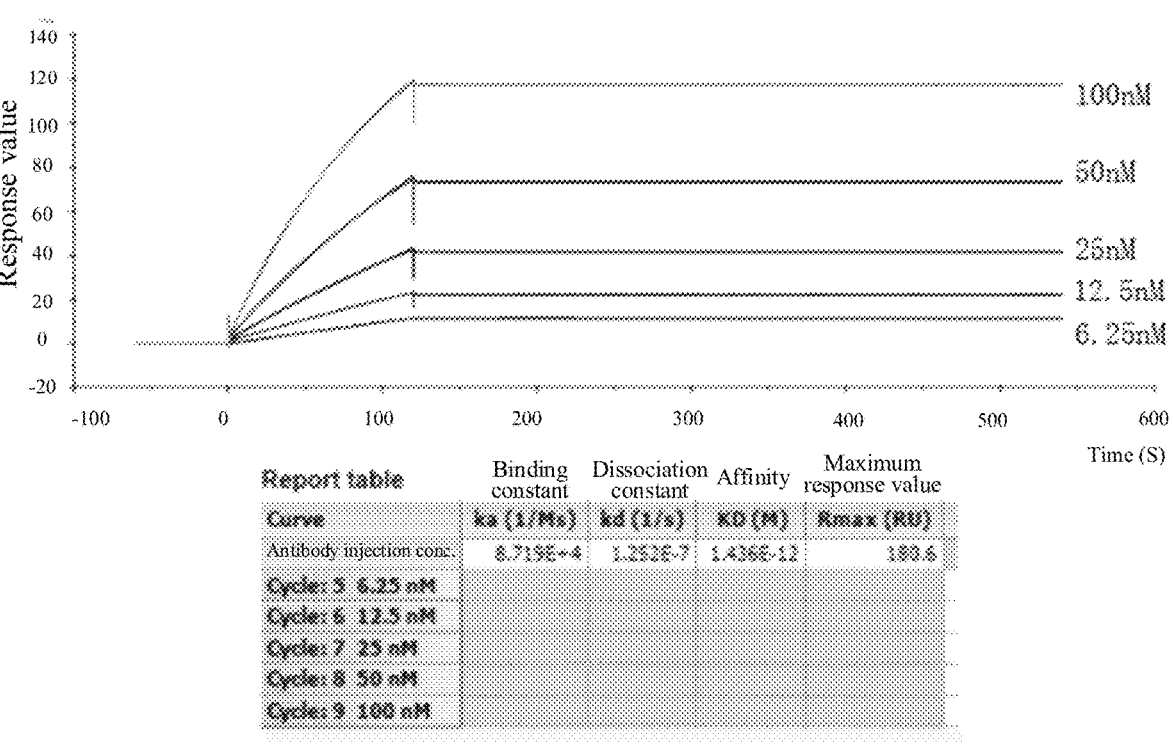
FIG. 9 is a graph showing the results of SPR assay for VHH-Z3-Fc affinity according to some embodiments of the present disclosure.

After the chip was activated, 500 nM PCSK9 antigen was added for reaction. The residual active carboxyl groups were washed off by adding 150 μL of 1M ethanolamine hydrochloride; after gradient dilution of PCSK9 antibody, 360 μL antibody was added at a rate of 25 μL/min for binding for 120 s and dissociating for 400 s; after obtaining the data, the results were processed and shown in FIGS. 7, 8, and 9 below, showing the signal intensity when the binding site of the antibody was occupied by the antigen, where KD (M) is the dissociation constant of the antigen-antibody interaction, indicating that each antibody of PCSK9 has good interaction with the PCSK9 antigen, and has the value for further development.

Figure 10:
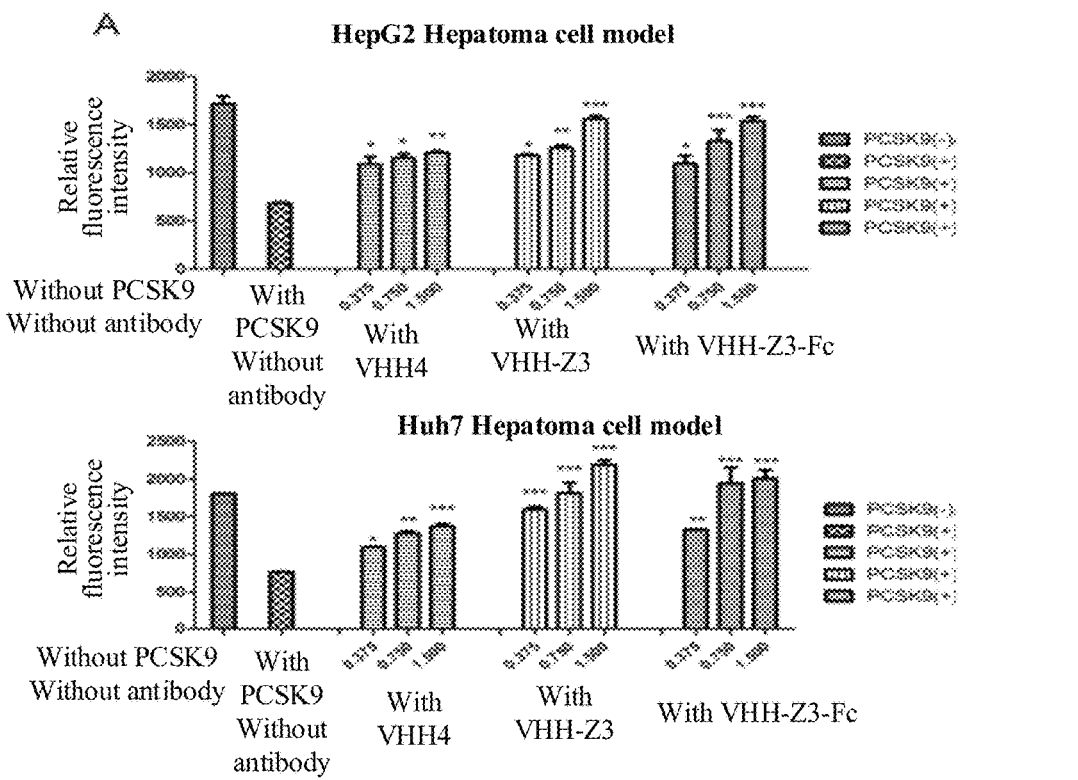
FIG. 10 is a graph showing the in vitro pharmacodynamic validation results for the PCSK9 antibodies according to some embodiments of the present disclosure.

Example 5 In Vitro Pharmacodynamic Validation of PCSK9 Antibody on Cancer Cell Model The cultured Huh7 and HepG2 cells were plated in 96-well plates (Corning, USA) at a cell density of $5 \times 10^5$ cells/well (cells were resuspended with fresh DMEM containing 10% fetal bovine serum). The cells were cultured at 37° C. for 18 to 20 h, washed with D-PBS (Gibco, USA), and transferred to serum-free culture system. A total of five groups were designed for the experiment. The first group was blank control (without hPCSK9 and antibody). The second group was negative control (only hPCSK9 was added at a concentration of 0.08 μM. The hPCSK9 (at a concentration of 0.08 μM) protein and two other sets of antibodies (VHH-Z3 and VHH-Z3-Fc, at concentrations of 0.75 μM, 0.375 μM, and 1.5 μM, respectively), pre-heated to 37° C., were then added to the cells. The cells were cultured for 1 h at 37° C., 10 μL of LDL-BIODIPY (Invitrogen, USA) was added to the cells (at a concentration of 6 μg/mL) and the cells were further cultured for 3 h at 37° C. The culture solution was washed three times with D-PBS (Gibco brand, USA), and relative fluorescence intensity was measured with a fluorescence microplate reader M1000 PRO (Tecan, Switzerland). Fluorescence intensity can reflect the metabolic level of low density lipoprotein LDL. The results are shown in FIG. 10. In the two groups of hepatoma cell models, the addition of each of VHH4, VHH-Z3, and VHH-Z3-Fc antibodies blocked the binding of PCSK9 to LDLR, thereby promoting the absorption of LDLC by LDLR on the cell surface.

Figure 11:
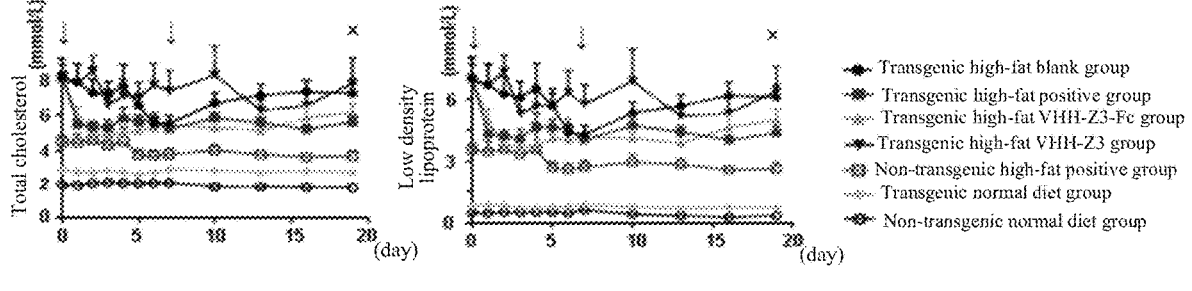
FIG. 11 is a graph showing the in vivo pharmacodynamic validation results of the PCSK9 antibodies according to some embodiments of the present disclosure.

Example 6 In Vivo Pharmacodynamic Validation of the PCSK9 Antibody in Transgenic Rats The animals for pharmacodynamic experiments were divided into seven groups with six rats in each group, among which five groups were hPCSK9 transgenic rats (Tg+rats) and two groups were normal control rats. hPCSK9 transgenic rats were obtained by randomly inserting the hPCSK9 gene into the genomes of zygotes of normal rats. Successfully transgenic rats were verified for the correct insertion of the hPCSK9 gene by PCR. These Tg+ rats developed hyperlipidemia symptoms after 8 weeks of high-fat diet induction. Of the five groups of transgenic rats, the first four groups continued on a high-fat diet and were injected with PBS, commercially available Repatha monoclonal antibody (Evolocumab), VHH-Z3, and VHH-Z3-Fc at the tail vein (injection dose of 20 mg/Kg), respectively. The four group were sequentially named as transgenic high-fat blank group, transgenic high-fat positive group, transgenic high-fat VHH-Z3 group, and transgenic high-fat VHH-Z3-Fc group, and the remaining group of transgenic rats was fed with normal diet. Two control groups of normal rats were also set, among which the first group was fed with non-transgenic normal diet, and the second group was fed with non-transgenic high-fat diet, injected with commercially available Repatha monoclonal antibody, and named as non-transgenic high-fat positive group. The rats were injected on days 0 to 7 and tested on day 19. Blood samples were collected, and levels of total cholesterol (CHOL) and liver low density lipoprotein were measured by an automated biochemical analyzer (Bs-600, Mindray, China), and the results are shown in FIG. 11. Compared with the control group, the hPCSK9 hyperlipidemia rats, after being administrated with positive drugs, had significantly reduced levels of CHOL and LDL-C, which maintained until the end of the experiment. The test drug VHH-Z3-Fc also significantly reduced levels of CHOL and LDL-C in hPCSK9 hyperlipidemic rat model, and the hypolipidemic effect was slightly better than that of the positive drug group between Day 2 and Day 13 after administration. There was no significant effect of test drug VHH-Z3 on the levels of CHOL and LDL-C in hPCSK9 hyperlipidemia rat model during the whole administration period.

In this disclosure, description with reference to the term "one embodiment", "some embodiments", "an example", "a specific example" or "some examples" or the like means that a specific feature, structure, material or characteristic described in conjunction with the example(s) or example(s) are included in at least one embodiment or example of the present disclosure. In this specification, illustrative expressions of these terms do not necessarily refer to the same embodiment or example. Moreover, the specific feature, structure, material, or characteristic described may be combined in any suitable manner in any one or more embodiments or examples. In addition, without mutual contradiction, those skilled in the art may incorporate and combine different embodiments or examples and features of the different embodiments or examples described in this specification.

Although the embodiments of the present disclosure have been illustrated and described, it should be understood that the embodiments are exemplary and should not be construed as limiting the present disclosure, and persons of ordinary skill in the art may make various changes, modifications, replacements and variations to the above embodiments within the scope of the present disclosure.

What is claimed is:

1. An antibody capable of specifically recognizing PCSK9 or an antigen-binding fragment thereof, wherein the antibody comprises a heavy chain variable region having amino sequence SEQ ID NO: 20.

2. The antibody or the antigen-binding fragment thereof according to claim 1, wherein the antibody further comprises a heavy chain constant region, at least a part of the heavy chain constant region is derived from at least one of a murine antibody, a human antibody, a primate antibody, or a mutant thereof.

3. The antibody or the antigen-binding fragment thereof according to claim 2, wherein the heavy chain constant region of the antibody is derived from a human IgG antibody or a mutant thereof.

4. The antibody or the antigen-binding fragment thereof according to claim 2, wherein the heavy chain constant region of the antibody is derived from a human IgG4.

5. The antibody or the antigen-binding fragment thereof according to claim 4, wherein a constant region of the antibody constant region has a full-length sequence shown in SEQ ID NO: 26.

6. The antibody or the antigen-binding fragment thereof according to claim 5, wherein the antibody has a heavy chain having amino acid sequence SEQ ID NO: 31.

7. The antibody or the antigen-binding fragment thereof according to claim 1, wherein the antibody is a small molecule antibody, wherein the small molecule antibody comprises at least one of a VHH antibody, an Fab antibody, an Fv antibody, or a minimal recognition unit.

8. A nucleic acid molecule, encoding the antibody or the antigen-binding fragment thereof according to claim 1.

9. The nucleic acid molecule according to claim 8, wherein the nucleic acid molecule is DNA having nucleotide in SEQ ID NO: 41.

10. An expression vector, carrying the nucleic acid molecule according to claim 9.

11. The expression vector according to claim 10, wherein the expression vector is a prokaryotic expression vector.

12. A recombinant cell, expressing the antibody or the antigen-binding fragment thereof according to claim 1.

13. The recombinant cell according to claim 12, wherein the recombinant cell is a prokaryotic cell.

14. A pharmaceutical composition, comprising the antibody according to claim 1.

15. A pharmaceutical composition, comprising the nucleic acid molecule according to claim 8.

16. A pharmaceutical composition, comprising the expression vector according to claim 10.

17. A pharmaceutical composition, comprising the recombinant cell according to claim 12.

18. A method for preventing or treating PCSK9-related diseases, comprising administering the antibody according to claim 1 to a subject in need thereof.

19. The method according to claim 18, wherein the PCSK9-related diseases comprise hyperlipidemia, hypercholesterolemia, and conditions caused by atherosclerosis.

20. A kit for detecting PCSK9, the kit comprising the antibody according to claim 1.

* * * * *

```
                         SEQUENCE LISTING

Sequence total quantity: 55
SEQ ID NO: 1              moltype = AA  length = 8
FEATURE                  Location/Qualifiers
REGION                   1..8
                         note = Sequence of CDR1
source                   1..8
                         mol_type = protein
                         organism = synthetic construct
SEQUENCE: 1
GYTYSSNC                                                        8

SEQ ID NO: 2              moltype = AA  length = 8
FEATURE                  Location/Qualifiers
REGION                   1..8
                         note = Sequence of CDR2
source                   1..8
                         mol_type = protein
                         organism = synthetic construct
SEQUENCE: 2
IYIGGGST                                                        8

SEQ ID NO: 3              moltype = AA  length = 12
FEATURE                  Location/Qualifiers
REGION                   1..12
                         note = Sequence of CDR3
source                   1..12
                         mol_type = protein
                         organism = synthetic construct
SEQUENCE: 3
AVGCQGLVDF GY                                                   12

SEQ ID NO: 4              moltype = AA  length = 25
FEATURE                  Location/Qualifiers
REGION                   1..25
                         note = Heavy chain framework region sequence
source                   1..25
                         mol_type = protein
                         organism = synthetic construct
SEQUENCE: 4
QVQLQESGGG SVQAGGSLRL SCTVS                                     25

SEQ ID NO: 5              moltype = AA  length = 17
FEATURE                  Location/Qualifiers
REGION                   1..17
                         note = Heavy chain framework region sequence
source                   1..17
                         mol_type = protein
                         organism = synthetic construct
SEQUENCE: 5
MGWFRQAPGK EHEGVAS                                              17

SEQ ID NO: 6              moltype = AA  length = 38
FEATURE                  Location/Qualifiers
REGION                   1..38
                         note = Heavy chain framework region sequence
source                   1..38
                         mol_type = protein
                         organism = synthetic construct
SEQUENCE: 6
YYADSVKGRF TISQDNAKNT VYLQMNSLKP EDTAMYYC                       38

SEQ ID NO: 7              moltype = AA  length = 11
FEATURE                  Location/Qualifiers
REGION                   1..11
                         note = Heavy chain framework region sequence
source                   1..11
                         mol_type = protein
                         organism = synthetic construct
SEQUENCE: 7
WDQGTQVTVS S                                                    11
```

-continued

```
SEQ ID NO: 8          moltype = AA  length = 25
FEATURE               Location/Qualifiers
REGION                1..25
                      note = Heavy chain framework region sequence
source                1..25
                      mol_type = protein
                      organism = synthetic construct
SEQUENCE: 8
EVQLLESGGG LVQPGGSLRL SCAAS                                  25

SEQ ID NO: 9          moltype = AA  length = 17
FEATURE               Location/Qualifiers
REGION                1..17
                      note = Heavy chain framework region sequence
source                1..17
                      mol_type = protein
                      organism = synthetic construct
SEQUENCE: 9
MGWVRQAPGK GLEWVSS                                           17

SEQ ID NO: 10         moltype = AA  length = 38
FEATURE               Location/Qualifiers
REGION                1..38
                      note = Heavy chain framework region sequence
source                1..38
                      mol_type = protein
                      organism = synthetic construct
SEQUENCE: 10
YYADSVKGRF TISRDNSKNT LYLQMNSLRA EDTAVYYC                    38

SEQ ID NO: 11         moltype = AA  length = 25
FEATURE               Location/Qualifiers
REGION                1..25
                      note = Heavy chain framework region sequence
source                1..25
                      mol_type = protein
                      organism = synthetic construct
SEQUENCE: 11
EVQLLESGGG LVQPGGSLRL SCTVS                                  25

SEQ ID NO: 12         moltype = AA  length = 17
FEATURE               Location/Qualifiers
REGION                1..17
                      note = Heavy chain framework region sequence
source                1..17
                      mol_type = protein
                      organism = synthetic construct
SEQUENCE: 12
MGWFRQAPGK EHEGVSS                                           17

SEQ ID NO: 13         moltype = AA  length = 38
FEATURE               Location/Qualifiers
REGION                1..38
                      note = Heavy chain framework region sequence
source                1..38
                      mol_type = protein
                      organism = synthetic construct
SEQUENCE: 13
YYADSVKGRF TISQDNSKNT LYLQMNSLRA EDTAVYYC                    38

SEQ ID NO: 14         moltype = AA  length = 38
FEATURE               Location/Qualifiers
REGION                1..38
                      note = Heavy chain framework region sequence
source                1..38
                      mol_type = protein
                      organism = synthetic construct
SEQUENCE: 14
YYADSVKGRF TISQDNAKNT LYLQMNSLRA EDTAVYYC                    38

SEQ ID NO: 15         moltype = AA  length = 38
FEATURE               Location/Qualifiers
REGION                1..38
                      note = Heavy chain framework region sequence
source                1..38
                      mol_type = protein
                      organism = synthetic construct
SEQUENCE: 15
YYADSVKGRF TISQDNSKNT VYLQMNSLRA EDTAVYYC                    38
```

-continued

```
SEQ ID NO: 16              moltype = AA  length = 119
FEATURE                    Location/Qualifiers
REGION                     1..119
                           note = Heavy chain variable region sequence
source                     1..119
                           mol_type = protein
                           organism = synthetic construct
SEQUENCE: 16
QVQLQESGGG SVQAGGSLRL SCTVSGYTYS SNCMGWFRQA PGKEHEGVAS IYIGGGSTYY  60
ADSVKGRFTI SQDNAKNTVY LQMNSLKPED TAMYYCAVGC QGLVDFGYWD QGTQVTVSS   119

SEQ ID NO: 17              moltype = AA  length = 119
FEATURE                    Location/Qualifiers
REGION                     1..119
                           note = Heavy chain variable region sequence
source                     1..119
                           mol_type = protein
                           organism = synthetic construct
SEQUENCE: 17
EVQLLESGGG LVQPGGSLRL SCAASGYTYS SNCMGWVRQA PGKGLEWVSS IYIGGGSTYY  60
ADSVKGRFTI SRDNSKNTLY LQMNSLRAED TAVYYCAVGC QGLVDFGYWD QGTQVTVSS   119

SEQ ID NO: 18              moltype = AA  length = 119
FEATURE                    Location/Qualifiers
REGION                     1..119
                           note = Heavy chain variable region sequence
source                     1..119
                           mol_type = protein
                           organism = synthetic construct
SEQUENCE: 18
EVQLLESGGG LVQPGGSLRL SCTVSGYTYS SNCMGWFRQA PGKEHEGVSS IYIGGGSTYY  60
ADSVKGRFTI SRDNSKNTLY LQMNSLRAED TAVYYCAVGC QGLVDFGYWD QGTQVTVSS   119

SEQ ID NO: 19              moltype = AA  length = 119
FEATURE                    Location/Qualifiers
REGION                     1..119
                           note = Heavy chain variable region sequence
source                     1..119
                           mol_type = protein
                           organism = synthetic construct
SEQUENCE: 19
EVQLLESGGG LVQPGGSLRL SCAASGYTYS SNCMGWFRQA PGKEHEGVSS IYIGGGSTYY  60
ADSVKGRFTI SQDNSKNTLY LQMNSLRAED TAVYYCAVGC QGLVDFGYWD QGTQVTVSS   119

SEQ ID NO: 20              moltype = AA  length = 119
FEATURE                    Location/Qualifiers
REGION                     1..119
                           note = Heavy chain variable region sequence
source                     1..119
                           mol_type = protein
                           organism = synthetic construct
SEQUENCE: 20
EVQLLESGGG LVQPGGSLRL SCAASGYTYS SNCMGWFRQA PGKEHEGVAS IYIGGGSTYY  60
ADSVKGRFTI SQDNAKNTLY LQMNSLRAED TAVYYCAVGC QGLVDFGYWD QGTQVTVSS   119

SEQ ID NO: 21              moltype = AA  length = 119
FEATURE                    Location/Qualifiers
REGION                     1..119
                           note = Heavy chain variable region sequence
source                     1..119
                           mol_type = protein
                           organism = synthetic construct
SEQUENCE: 21
EVQLLESGGG LVQPGGSLRL SCAASGYTYS SNCMGWFRQA PGKEHEGVSS IYIGGGSTYY  60
ADSVKGRFTI SQDNAKNTLY LQMNSLRAED TAVYYCAVGC QGLVDFGYWD QGTQVTVSS   119

SEQ ID NO: 22              moltype = AA  length = 119
FEATURE                    Location/Qualifiers
REGION                     1..119
                           note = Heavy chain variable region sequence
source                     1..119
                           mol_type = protein
                           organism = synthetic construct
SEQUENCE: 22
EVQLLESGGG LVQPGGSLRL SCAASGYTYS SNCMGWFRQA PGKEHEGVSS IYIGGGSTYY  60
ADSVKGRFTI SQDNSKNTVY LQMNSLRAED TAVYYCAVGC QGLVDFGYWD QGTQVTVSS   119

SEQ ID NO: 23              moltype = AA  length = 119
```

```
FEATURE               Location/Qualifiers
REGION                1..119
                      note = Heavy chain variable region sequence
source                1..119
                      mol_type = protein
                      organism = synthetic construct
SEQUENCE: 23
EVQLLESGGG LVQPGGSLRL SCTVSGYTYS SNCMGWFRQA PGKEHEGVSS IYIGGGSTYY    60
ADSVKGRFTI SQDNSKNTLY LQMNSLRAED TAVYYCAVGC QGLVDFGYWD QGTQVTVSS     119

SEQ ID NO: 24         moltype = AA  length = 119
FEATURE               Location/Qualifiers
REGION                1..119
                      note = Heavy chain variable region sequence
source                1..119
                      mol_type = protein
                      organism = synthetic construct
SEQUENCE: 24
EVQLLESGGG LVQPGGSLRL SCTVSGYTYS SNCMGWFRQA PGKEHEGVSS IYIGGGSTYY    60
ADSVKGRFTI SQDNAKNTLY LQMNSLRAED TAVYYCAVGC QGLVDFGYWD QGTQVTVSS     119

SEQ ID NO: 25         moltype = AA  length = 119
FEATURE               Location/Qualifiers
REGION                1..119
                      note = Heavy chain variable region sequence
source                1..119
                      mol_type = protein
                      organism = synthetic construct
SEQUENCE: 25
EVQLLESGGG LVQPGGSLRL SCAASGYTYS SNCMGWFRQA PGKEHEGVSS IYIGGGSTYY    60
ADSVKGRFTI SQDNAKNTLY LQMNSLRAED TAVYYCAVGC QGLVDFGYWD QGTQVTVSS     119

SEQ ID NO: 26         moltype = AA  length = 224
FEATURE               Location/Qualifiers
REGION                1..224
                      note = Full-length sequence of antibody constant region
source                1..224
                      mol_type = protein
                      organism = synthetic construct
SEQUENCE: 26
PPCPSCPAPE FLGGPSVFLF PPKPKDTLMI SRTPEVTCVV VDVSQEDPEV QFNWYVDGVE    60
VHNAKTKPRE EQFNSTYRVV SVLTVLHQDW LNGKEYKCKV SNKGLPSSIE KTISKAKGQP   120
REPQVYTLPP SQEEMTKNQV SLTCLVKGFY PSDIAVEWES NGQPENNYKT TPPVLDSDGS   180
FFLYSRLTVD KSRWQEGNVF SCSVMHEALH NHYTQKSLSL SPGK                    224

SEQ ID NO: 27         moltype = AA  length = 343
FEATURE               Location/Qualifiers
REGION                1..343
                      note = Heavy chain sequence
source                1..343
                      mol_type = protein
                      organism = synthetic construct
SEQUENCE: 27
QVQLQESGGG SVQAGGSLRL SCTVSGYTYS SNCMGWFRQA PGKEHEGVAS IYIGGGSTYY    60
ADSVKGRFTI SQDNAKNTVY LQMNSLKPED TAMYYCAVGC QGLVDFGYWD QGTQVTVSSP   120
PCPSCPAPEF LGGPSVFLFP PKPKDTLMIS RTPEVTCVVV DVSQEDPEVQ FNWYVDGVEV   180
HNAKTKPREE QFNSTYRVVS VLTVLHQDWL NGKEYKCKVS NKGLPSSIEK TISKAKGQPR   240
EPQVYTLPPS QEEMTKNQVS LTCLVKGFYP SDIAVEWESN GQPENNYKTT PPVLDSDGSF   300
FLYSRLTVDK SRWQEGNVFS CSVMHEALHN HYTQKSLSLS PGK                     343

SEQ ID NO: 28         moltype = AA  length = 343
FEATURE               Location/Qualifiers
REGION                1..343
                      note = Heavy chain sequence
source                1..343
                      mol_type = protein
                      organism = synthetic construct
SEQUENCE: 28
EVQLLESGGG LVQPGGSLRL SCAASGYTYS SNCMGWVRQA PGKGLEWVSS IYIGGGSTYY    60
ADSVKGRFTI SRDNSKNTLY LQMNSLRAED TAVYYCAVGC QGLVDFGYWD QGTQVTVSSP   120
PCPSCPAPEF LGGPSVFLFP PKPKDTLMIS RTPEVTCVVV DVSQEDPEVQ FNWYVDGVEV   180
HNAKTKPREE QFNSTYRVVS VLTVLHQDWL NGKEYKCKVS NKGLPSSIEK TISKAKGQPR   240
EPQVYTLPPS QEEMTKNQVS LTCLVKGFYP SDIAVEWESN GQPENNYKTT PPVLDSDGSF   300
FLYSRLTVDK SRWQEGNVFS CSVMHEALHN HYTQKSLSLS PGK                     343

SEQ ID NO: 29         moltype = AA  length = 343
FEATURE               Location/Qualifiers
REGION                1..343
                      note = Heavy chain sequence
```

-continued

```
source                   1..343
                         mol_type = protein
                         organism = synthetic construct
SEQUENCE: 29
EVQLLESGGG LVQPGGSLRL SCTVSGYTYS SNCMGWFRQA PGKEHEGVSS IYIGGGSTYY    60
ADSVKGRFTI SRDNSKNTLY LQMNSLRAED TAVYYCAVGC QGLVDFGYWD QGTQVTVSSP   120
PCPSCPAPEF LGGPSVFLFP PKPKDTLMIS RTPEVTCVVV DVSQEDPEVQ FNWYVDGVEV   180
HNAKTKPREE QFNSTYRVVS VLTVLHQDWL NGKEYKCKVS NKGLPSSIEK TISKAKGQPR   240
EPQVYTLPPS QEEMTKNQVS LTCLVKGFYP SDIAVEWESN GQPENNYKTT PPVLDSDGSF   300
FLYSRLTVDK SRWQEGNVFS CSVMHEALHN HYTQKSLSLS PGK                     343

SEQ ID NO: 30            moltype = AA   length = 343
FEATURE                  Location/Qualifiers
REGION                   1..343
                         note = Heavy chain sequence
source                   1..343
                         mol_type = protein
                         organism = synthetic construct
SEQUENCE: 30
EVQLLESGGG LVQPGGSLRL SCAASGYTYS SNCMGWFRQA PGKEHEGVSS IYIGGGSTYY    60
ADSVKGRFTI SQDNSKNTLY LQMNSLRAED TAVYYCAVGC QGLVDFGYWD QGTQVTVSPP   120
CPSCPAPEFL GGPSVFLFPP KPKDTLMISR TPEVTCVVVD VSQEDPEVQF NWYVDGVEVH   180
NAKTKPREEQ FNSTYRVVSV LTVLHQDWLN GKEYKCKVSN KGLPSSIEKT ISKAKGQPRE   240
PQVYTLPPSQ EEMTKNQVSL TCLVKGFYPS DIAVEWESNG QPENNYKTTP PVLDSDGSFF   300
LYSRLTVDKS RWQEGNVFSC SVMHEALHNH YTQKSLSLSP GKS                     343

SEQ ID NO: 31            moltype = AA   length = 343
FEATURE                  Location/Qualifiers
REGION                   1..343
                         note = Heavy chain sequence
source                   1..343
                         mol_type = protein
                         organism = synthetic construct
SEQUENCE: 31
EVQLLESGGG LVQPGGSLRL SCAASGYTYS SNCMGWFRQA PGKEHEGVAS IYIGGGSTYY    60
ADSVKGRFTI SQDNAKNTLY LQMNSLRAED TAVYYCAVGC QGLVDFGYWD QGTQVTVSSP   120
PCPSCPAPEF LGGPSVFLFP PKPKDTLMIS RTPEVTCVVV DVSQEDPEVQ FNWYVDGVEV   180
HNAKTKPREE QFNSTYRVVS VLTVLHQDWL NGKEYKCKVS NKGLPSSIEK TISKAKGQPR   240
EPQVYTLPPS QEEMTKNQVS LTCLVKGFYP SDIAVEWESN GQPENNYKTT PPVLDSDGSF   300
FLYSRLTVDK SRWQEGNVFS CSVMHEALHN HYTQKSLSLS PGK                     343

SEQ ID NO: 32            moltype = AA   length = 343
FEATURE                  Location/Qualifiers
REGION                   1..343
                         note = Heavy chain sequence
source                   1..343
                         mol_type = protein
                         organism = synthetic construct
SEQUENCE: 32
EVQLLESGGG LVQPGGSLRL SCAASGYTYS SNCMGWFRQA PGKEHEGVSS IYIGGGSTYY    60
ADSVKGRFTI SQDNAKNTLY LQMNSLRAED TAVYYCAVGC QGLVDFGYWD QGTQVTVSSP   120
PCPSCPAPEF LGGPSVFLFP PKPKDTLMIS RTPEVTCVVV DVSQEDPEVQ FNWYVDGVEV   180
HNAKTKPREE QFNSTYRVVS VLTVLHQDWL NGKEYKCKVS NKGLPSSIEK TISKAKGQPR   240
EPQVYTLPPS QEEMTKNQVS LTCLVKGFYP SDIAVEWESN GQPENNYKTT PPVLDSDGSF   300
FLYSRLTVDK SRWQEGNVFS CSVMHEALHN HYTQKSLSLS PGK                     343

SEQ ID NO: 33            moltype = AA   length = 343
FEATURE                  Location/Qualifiers
REGION                   1..343
                         note = Heavy chain sequence
source                   1..343
                         mol_type = protein
                         organism = synthetic construct
SEQUENCE: 33
EVQLLESGGG LVQPGGSLRL SCAASGYTYS SNCMGWFRQA PGKEHEGVSS IYIGGGSTYY    60
ADSVKGRFTI SQDNSKNTVY LQMNSLRAED TAVYYCAVGC QGLVDFGYWD QGTQVTVSSP   120
PCPSCPAPEF LGGPSVFLFP PKPKDTLMIS RTPEVTCVVV DVSQEDPEVQ FNWYVDGVEV   180
HNAKTKPREE QFNSTYRVVS VLTVLHQDWL NGKEYKCKVS NKGLPSSIEK TISKAKGQPR   240
EPQVYTLPPS QEEMTKNQVS LTCLVKGFYP SDIAVEWESN GQPENNYKTT PPVLDSDGSF   300
FLYSRLTVDK SRWQEGNVFS CSVMHEALHN HYTQKSLSLS PGK                     343

SEQ ID NO: 34            moltype = AA   length = 343
FEATURE                  Location/Qualifiers
REGION                   1..343
                         note = Heavy chain sequence
source                   1..343
                         mol_type = protein
                         organism = synthetic construct
SEQUENCE: 34
```

```
EVQLLESGGG LVQPGGSLRL SCTVSGYTYS SNCMGWFRQA PGKEHEGVSS IYIGGGSTYY   60
ADSVKGRFTI SQDNSKNTLY LQMNSLRAED TAVYYCAVGC QGLVDFGYWD QGTQVTVSSP  120
PCPSCPAPEF LGGPSVFLFP PKPKDTLMIS RTPEVTCVVV DVSQEDPEVQ FNWYVDGVEV  180
HNAKTKPREE QFNSTYRVVS VLTVLHQDWL NGKEYKCKVS NKGLPSSIEK TISKAKGQPR  240
EPQVYTLPPS QEEMTKNQVS LTCLVKGFYP SDIAVEWESN GQPENNYKTT PPVLDSDGSF  300
FLYSRLTVDK SRWQEGNVFS CSVMHEALHN HYTQKSLSLS PGK                   343

SEQ ID NO: 35          moltype = AA  length = 343
FEATURE                Location/Qualifiers
REGION                 1..343
                       note = Heavy chain sequence
source                 1..343
                       mol_type = protein
                       organism = synthetic construct
SEQUENCE: 35
EVQLLESGGG LVQPGGSLRL SCTVSGYTYS SNCMGWFRQA PGKEHEGVSS IYIGGGSTYY   60
ADSVKGRFTI SQDNAKNTLY LQMNSLRAED TAVYYCAVGC QGLVDFGYWD QGTQVTVSSP  120
PCPSCPAPEF LGGPSVFLFP PKPKDTLMIS RTPEVTCVVV DVSQEDPEVQ FNWYVDGVEV  180
HNAKTKPREE QFNSTYRVVS VLTVLHQDWL NGKEYKCKVS NKGLPSSIEK TISKAKGQPR  240
EPQVYTLPPS QEEMTKNQVS LTCLVKGFYP SDIAVEWESN GQPENNYKTT PPVLDSDGSF  300
FLYSRLTVDK SRWQEGNVFS CSVMHEALHN HYTQKSLSLS PGK                   343

SEQ ID NO: 36          moltype = AA  length = 343
FEATURE                Location/Qualifiers
REGION                 1..343
                       note = Heavy chain sequence
source                 1..343
                       mol_type = protein
                       organism = synthetic construct
SEQUENCE: 36
EVQLLESGGG LVQPGGSLRL SCAASGYTYS SNCMGWFRQA PGKEHEGVSS IYIGGGSTYY   60
ADSVKGRFTI SQDNAKNTLY LQMNSLRAED TAVYYCAVGC QGLVDFGYWD QGTQVTVSSP  120
PCPSCPAPEF LGGPSVFLFP PKPKDTLMIS RTPEVTCVVV DVSQEDPEVQ FNWYVDGVEV  180
HNAKTKPREE QFNSTYRVVS VLTVLHQDWL NGKEYKCKVS NKGLPSSIEK TISKAKGQPR  240
EPQVYTLPPS QEEMTKNQVS LTCLVKGFYP SDIAVEWESN GQPENNYKTT PPVLDSDGSF  300
FLYSRLTVDK SRWQEGNVFS CSVMHEALHN HYTQKSLSLS PGK                   343

SEQ ID NO: 37          moltype = DNA  length = 357
FEATURE                Location/Qualifiers
misc_feature           1..357
                       note = Nucleic acid molecular sequence
source                 1..357
                       mol_type = other DNA
                       organism = synthetic construct
SEQUENCE: 37
caagtccagt tgcaggaatc cggtggagga tctgtccagg ccggtggctc tttacgtctt   60
agttgcactg tgtccggcta tacgtacagt tccaactgca tgggttggtt cagacaagct  120
cccggaaagg agcacgaggg agtagcctca atttacatcg gcggaggcag tacctattat  180
gcagattccg tcaaaggtcg tttttacgatc tcacaggata acgcaaagaa cacggtctac  240
ctgcaaatga acagtctgaa gcccgaagac acggcaatgt attattgcgc cgtgggttgc  300
caaggtttgg tggacttcgg ctactgggac cagggaaccc aggtcactgt atcatcc     357

SEQ ID NO: 38          moltype = DNA  length = 357
FEATURE                Location/Qualifiers
misc_feature           1..357
                       note = Nucleic acid molecular sequence
source                 1..357
                       mol_type = other DNA
                       organism = synthetic construct
SEQUENCE: 38
gaagttcagc tgttggaatc aggaggtggc cttgtacagc ctggcggcag tcttcgtctg   60
tcttgtgccg cctctggata cacttactct agtaattgca tgggttgggt caggcaggcc  120
ccaggaaaag gattggagtg ggtgtcatcc atttacatcg gaggcggatc tacttactac  180
gccgactccg tgaagggcag gttcacgatc tccagagaca actccaaaaa tacgttgtac  240
ttgcagatga acagtcttag agctgaggac accgcagttt actactgtgc cgtcggttgc  300
cagggtctag ttgactttgg ttactgggat cagggcactc aggttacggt ttcatcc     357

SEQ ID NO: 39          moltype = DNA  length = 357
FEATURE                Location/Qualifiers
misc_feature           1..357
                       note = Nucleic acid molecular sequence
source                 1..357
                       mol_type = other DNA
                       organism = synthetic construct
SEQUENCE: 39
gaagtccagc ttttggaatc aggcggtgga ctagttcagc ctggtggaag tctgaggctg   60
tcctgcacag tttccggtta tacgtactcc agtaattgca tgggctggtt cagacaggcc  120
ccaggtaagg agcacgaagg tgtatcttct atttacattg gtggcggatc tacttactac  180
gccgattcag tgaagggccg ttttaccatc tccagggaca atagtaaaaa cacgttgtac  240
```

-continued

```
ctgcagatga acagtttaag agcagaagac actgctgtct actactgcgc cgtgggttgc    300
cagggcttgg ttgacttcgg ctactgggac caaggaacgc aggtcaccgt atctagt       357

SEQ ID NO: 40           moltype = DNA   length = 357
FEATURE                 Location/Qualifiers
misc_feature            1..357
                        note = Nucleic acid molecular sequence
source                  1..357
                        mol_type = other DNA
                        organism = synthetic construct
SEQUENCE: 40
gaagttcaat tacttgagag tggcggtggt ttggtgcagc caggcggctc cctgagactg    60
tcatgcgccg cttccggata cacgtattct tccaactgca tgggttggtt ccgtcaggct    120
cctggaaagg agcatgaagg tgtctcttca atctacatag gaggcggttc cacttactac    180
gcagactctg tgaagggccg ttttaccatc tcccaggata attccaagaa cacattgtac    240
ctgcaaatga acagtctacg tgccgaagac acagccgttt actactgcgc tgttggctgc    300
cagggccttg tggacttcgg ctattgggac caaggcacac aggtaacggt ttcatca       357

SEQ ID NO: 41           moltype = DNA   length = 357
FEATURE                 Location/Qualifiers
misc_feature            1..357
                        note = Nucleic acid molecular sequence
source                  1..357
                        mol_type = other DNA
                        organism = synthetic construct
SEQUENCE: 41
gaggtccagc ttcttgaatc aggcggtgga ctagtgcagc ctggcggctc attgaggttg    60
tcctgtgctg ccagtggcta cacgtactcc tccaactgta tgggctggtt taggcaagca    120
cccggtaaag agcacgaggg cgtagcctct atctacattg gcggaggatc tacctattac    180
gccgactccg tcaaaggccg tttcacgata tcccaggata acgctaagaa cacgctgtac    240
ttacaaatga actcactgag agctgaagac accgccgtgt attattgcgc cgttggttgt    300
caaggtcttg tcgactttgg atattgggat cagggtacgc aagtaaccgt ctcaagt       357

SEQ ID NO: 42           moltype = DNA   length = 357
FEATURE                 Location/Qualifiers
misc_feature            1..357
                        note = Nucleic acid molecular sequence
source                  1..357
                        mol_type = other DNA
                        organism = synthetic construct
SEQUENCE: 42
gaagttcagt tgctagagtc aggaggcggt ctagtccagc ccggtggatc tctgaggcta    60
agttgcgctg cctccggtta cacgtatagt tcaaactgta tgggatggtt tcgtcaagca    120
cctggtaaag agcacgaggg tgtgagttcc atttacatcg gcggtggcag tacatactac    180
gcagattccg ttaaaggcag atttacgatt tctcaggata acgccaaaaa cacactgtac    240
ctacaaatga acagtcttcg tgcagaggat accgcagtgt attattgcgc cgtcggatgc    300
caaggttttg tggacttcgg ctattgggat cagggcacgc aagttaccgt ctctagt       357

SEQ ID NO: 43           moltype = DNA   length = 357
FEATURE                 Location/Qualifiers
misc_feature            1..357
                        note = Nucleic acid molecular sequence
source                  1..357
                        mol_type = other DNA
                        organism = synthetic construct
SEQUENCE: 43
gaagtccaac ttctggagtc tggcggtggc ctggtacaac ctggaggctc acttaggcta    60
tcctgcgccg cttccggcta tacatattct tcaaactgta tgggctggtt tcgtcaggcc    120
ccagccaaag agcacgaggg agtatcatca atctacattg gtggcggtcc cacgtactac    180
gccgatagtg tgaaaggcag gttcaccatc tcccaggaca actccaagaa cactgtgtat    240
ctacaaatga attccctgag ggctgaagat accgccgtat attactgcgc tgttggctgc    300
cagggccttg ttgattttgg ctattgggac caggggcacac aggttacggt gtcttcc       357

SEQ ID NO: 44           moltype = DNA   length = 357
FEATURE                 Location/Qualifiers
misc_feature            1..357
                        note = Nucleic acid molecular sequence
source                  1..357
                        mol_type = other DNA
                        organism = synthetic construct
SEQUENCE: 44
gaggtccaac ttttggagtc tggaggagga ctggtccaac ctggaggctc cctgagactg    60
tcctgtactg tgtctggcta cacctactcc agcaactgta tgggctggtt cagacaggct    120
cctggcaagg aacatgaggg agtgtccagc atctacattg gaggaggcag cacctactat    180
gctgactctg tgaagggcag gttcaccatc agccaggaca acagcaagaa cacccctctac    240
ctccaaatga actccctgag ggctgaggac acagcagtct actactgtgc tgtgggctgt    300
cagggactgt tggactttgg ctactgggac caggggcaccc aggtgacagt gtcctcc       357

SEQ ID NO: 45           moltype = DNA   length = 357
```

-continued

```
FEATURE            Location/Qualifiers
misc_feature       1..357
                   note = Nucleic acid molecular sequence
source             1..357
                   mol_type = other DNA
                   organism = synthetic construct
SEQUENCE: 45
gaggtccaac ttttggagtc tggaggagga ctggtccaac ctggaggctc cctgagactg   60
tcctgtactg tgtctggcta cacctactcc agcaactgta tgggctggtt cagacaggct  120
cctggcaagg aacatgaggg agtgtccagc atctacattg gaggaggcag cacctactat  180
gctgactctg tgaagggcag gttcaccatc agccaggaca acgccaagaa caccctctac  240
ctccaaatga actccctgag ggctgaggac acagcagtct actactgtgc tgtgggctgt  300
cagggactgg tggactttgg ctactgggac cagggcaccc aggtgacagt gtcctcc     357

SEQ ID NO: 46       moltype = DNA   length = 357
FEATURE             Location/Qualifiers
misc_feature        1..357
                    note = Nucleic acid molecular sequence
source              1..357
                    mol_type = other DNA
                    organism = synthetic construct
SEQUENCE: 46
gaggtccaac ttttggagtc tggaggagga ctggtccaac ctggaggctc cctgagactg   60
tcctgtgctg cctctggcta cacctactcc agcaactgta tgggctggtt cagacaggct  120
cctggcaagg aacatgaggg agtgtccagc atctacattg gaggaggcag cacctactat  180
gctgactctg tgaagggcag gttcaccatc agccaggaca acgccaagaa caccctctac  240
ctccaaatga actccctgag ggctgaggac acagcagtct actactgtgc tgtgggctgt  300
cagggactgg tggactttgg ctactgggac cagggcaccc aggtgacagt gtcctcc     357

SEQ ID NO: 47       moltype = AA   length = 7
FEATURE             Location/Qualifiers
REGION              1..7
                    note = Sequence of a hinge region
source              1..7
                    mol_type = protein
                    organism = synthetic construct
SEQUENCE: 47
PPCPSCP                                                              7

SEQ ID NO: 48       moltype = AA   length = 110
FEATURE             Location/Qualifiers
REGION              1..110
                    note = Sequence of a constant CH2 region
source              1..110
                    mol_type = protein
                    organism = synthetic construct
SEQUENCE: 48
APEFLGGPSV FLFPPKPKDT LMISRTPEVT CVVVDVSQED PEVQFNWYVD GVEVHNAKTK   60
PREEQFNSTY RVVSVLTVLH QDWLNGKEYK CKVSNKGLPS SIEKTISKAK             110

SEQ ID NO: 49       moltype = AA   length = 107
FEATURE             Location/Qualifiers
REGION              1..107
                    note = Sequence of a constant region CH3 region
source              1..107
                    mol_type = protein
                    organism = synthetic construct
SEQUENCE: 49
GQPREPQVYT LPPSQEEMTK NQVSLTCLVK GFYPSDIAVE WESNGQPENN YKTTPPVLDS   60
DGSFFLYSRL TVDKSRWQEG NVFSCSVMHE ALHNHYTQKS LSLSPGK                107

SEQ ID NO: 50       moltype = DNA   length = 23
FEATURE             Location/Qualifiers
misc_feature        1..23
                    note = Nest-PCR primer
source              1..23
                    mol_type = other DNA
                    organism = synthetic construct
SEQUENCE: 50
gtcctggctg ctcttctaca agg                                           23

SEQ ID NO: 51       moltype = DNA   length = 23
FEATURE             Location/Qualifiers
misc_feature        1..23
                    note = Nest-PCR primer
source              1..23
                    mol_type = other DNA
                    organism = synthetic construct
SEQUENCE: 51
```

-continued

```
ggtacgtgct gttgaactgt tcc                                          23

SEQ ID NO: 52          moltype = DNA  length = 20
FEATURE                Location/Qualifiers
misc_feature           1..20
                       note = Nest-PCR primer
source                 1..20
                       mol_type = other DNA
                       organism = synthetic construct
SEQUENCE: 52
tggtggcagg tccccaaggt                                              20

SEQ ID NO: 53          moltype = DNA  length = 23
FEATURE                Location/Qualifiers
misc_feature           1..23
                       note = Nest-PCR primer
source                 1..23
                       mol_type = other DNA
                       organism = synthetic construct
SEQUENCE: 53
ttcttggtgg cagtagccgc agt                                          23

SEQ ID NO: 54          moltype = DNA  length = 29
FEATURE                Location/Qualifiers
misc_feature           1..29
                       note = Nest-PCR primer
source                 1..29
                       mol_type = other DNA
                       organism = synthetic construct
SEQUENCE: 54
gatgtgcagc tgcaggagtc tggrggagg                                    29

SEQ ID NO: 55          moltype = DNA  length = 32
FEATURE                Location/Qualifiers
misc_feature           1..32
                       note = Nest-PCR primer
source                 1..32
                       mol_type = other DNA
                       organism = synthetic construct
SEQUENCE: 55
ctagtgcggc cgctggagac ggtgacctgg gt                                32
```